US012110330B2

(12) United States Patent
Brower et al.

(10) Patent No.: US 12,110,330 B2
(45) Date of Patent: Oct. 8, 2024

(54) COMPOSITIONS OF PROGRAMMED DEATH RECEPTOR 1 (PD-1) ANTIBODIES AND METHODS OF OBTAINING THE COMPOSITIONS THEREOF

(71) Applicant: Merck Sharp & Dohme LLC, Rahway, NJ (US)

(72) Inventors: Mark A. Brower, Bound Brook, NJ (US); Chung-Jr Huang, Berkeley Heights, NJ (US); Brian Wai Kwan, Parsippany, NJ (US); William Nicholas Napoli, Wayland, MA (US); Bhumit A. Patel, Edison, NJ (US); Nuno J. Dos Santos Pinto, Long Branch, NJ (US); Douglas Dennis Richardson, II, Collegeville, PA (US); Sen Xu, Pine Brook, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/586,109

(22) Filed: Jan. 27, 2022

(65) Prior Publication Data
US 2022/0251205 A1    Aug. 11, 2022

Related U.S. Application Data

(60) Provisional application No. 63/143,461, filed on Jan. 29, 2021.

(51) Int. Cl.
| | | |
|---|---|---|
| C07K 16/28 | (2006.01) | |
| A61K 39/00 | (2006.01) | |
| A61P 35/00 | (2006.01) | |
| C12N 15/85 | (2006.01) | |

(52) U.S. Cl.
CPC ........ C07K 16/2818 (2013.01); A61P 35/00 (2018.01); *A61K 2039/505* (2013.01); *C07K 2317/565* (2013.01); *C07K 2317/94* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 30,985 A | 12/1860 | Pye | |
| 4,560,655 A | 12/1985 | Baker | |
| 4,657,866 A | 4/1987 | Kumar | |
| 4,767,704 A | 8/1988 | Cleveland et al. | |
| 4,927,762 A | 5/1990 | Darfler | |
| 5,122,469 A | 6/1992 | Mather et al. | |
| 8,153,432 B2 | 4/2012 | Church et al. | |
| 8,354,509 B2 * | 1/2013 | Carven ................. | A61P 37/04 530/388.1 |
| 9,220,776 B2 | 12/2015 | Sharma et al. | |
| 9,228,208 B2 | 1/2016 | Frendewey et al. | |
| 9,428,767 B2 | 8/2016 | Minshull et al. | |
| 9,574,209 B2 | 2/2017 | Minshull et al. | |
| 9,580,697 B2 | 2/2017 | Minshull et al. | |
| 9,982,279 B1 | 5/2018 | Gill et al. | |
| 10,041,077 B2 | 8/2018 | Minshull et al. | |
| 11,014,986 B2 | 5/2021 | Reichert et al. | |
| 11,114,477 B2 | 9/2021 | Chen et al. | |
| 11,633,476 B2 | 4/2023 | Sharma et al. | |
| 2015/0079680 A1 | 3/2015 | Bradley et al. | |
| 2017/0204446 A1* | 7/2017 | Cattaneo ............ | B01D 15/3809 |
| 2018/0237524 A1 | 8/2018 | Reichert et al. | |
| 2020/0055938 A1 | 2/2020 | Desai et al. | |
| 2020/0147213 A1 | 5/2020 | Sharma et al. | |
| 2020/0262922 A1 | 8/2020 | Bhattacharya et al. | |
| 2020/0354453 A1 | 11/2020 | De et al. | |
| 2021/0234273 A1 | 7/2021 | Yuen et al. | |
| 2021/0317215 A1 | 10/2021 | Reichert et al. | |
| 2021/0380694 A1 | 12/2021 | Forrest, Jr. et al. | |
| 2022/0002410 A1 | 1/2022 | Antochshuk et al. | |
| 2022/0089738 A1 | 3/2022 | Krishnamachari et al. | |
| 2022/0378916 A1 | 12/2022 | Chu et al. | |
| 2023/0018939 A1 | 1/2023 | Brower et al. | |

FOREIGN PATENT DOCUMENTS

| | | |
|---|---|---|
| WO | 1987000195 A1 | 1/1987 |
| WO | 2008052101 A2 | 5/2008 |
| WO | 2014093661 A2 | 6/2014 |
| WO | 2017141173 A2 | 8/2017 |
| WO | 2018/204343 A1 † | 11/2018 |

(Continued)

OTHER PUBLICATIONS

Qian et al (Cell culture and gene transcription effects of copper sulfate on Chinese hamster ovary cell, Biotechnology Progress, Apr. 20, 2011), (Year: 2011).*
Abt, Brian et al., Design of a Pembrolizumab Manufacturing Plant Using Continuous Bioprocess Technology and Single-Use Bioreactors, University of Virginia, 2020, 1-118, N/A.
Al-Fageeh, Mohamed B. et al., The Cold-Shock Response in Cultured Mammalian Cells: Harnessing the Response for the Improvement of Recombinant Protein Production, Biotechnol. Bioeng., 2006, 829-835, 93.
Barnes, David et al., Methods for Growth of Cultured Cells in Serum-Free Medium, Anal. Biochem., 1980, 255-270, 102.
Bielser, Jean-Marc et al., Perfusion mammalian cell culture for recombinant protein manufacturing—A critical review, Biotechnology Advances, 2018, 1328-1340, 36.

(Continued)

*Primary Examiner* — Laura B Goddard
*Assistant Examiner* — Sarah A Alsomairy
(74) *Attorney, Agent, or Firm* — Li Su; Anna L. Cocuzzo

(57) ABSTRACT

The invention provides compositions of anti-PD-1 antibodies or antigen-binding fragments thereof with less than or equal to about 3.0% oxidation of Met105 in the CDRH3 heavy chain region, and methods of obtaining the purified compositions. The invention also provides compositions comprising anti-PD-1 antibody main species and acidic species thereof, wherein the amount of acidic species is about 1.0-12.0%.

32 Claims, 12 Drawing Sheets
Specification includes a Sequence Listing.

(56) References Cited

FOREIGN PATENT DOCUMENTS

| WO | 2018204368 | A1 |   | 11/2018 |            |
|----|------------|----|---|---------|------------|
| WO | WO-2019118426 | A1 | * | 6/2019 | C07K 16/241 |
| WO | 2020006831 | A1 |   | 1/2020  |            |
| WO | 2020068631 | A1 |   | 4/2020  |            |
| WO | 2020/097141 | A1 | † | 5/2020 |            |
| WO | 2020168315 | A1 |   | 8/2020  |            |
| WO | WO-2020252442 | A1 | * | 12/2020 | C12M 29/10 |
| WO | 2022026839 | A2 |   | 2/2022  |            |

OTHER PUBLICATIONS

Fiers, W. et al., Complete nucleotide sequence of SV40 DNA, Nature, 1978, 113-120, 273.

Grassi, Luigi et al., Susceptibility of protein therapeutics to spontaneous chemical modifications by oxidation, cyclization, and elimination reactions, Amino Acids, 2019, 1409-1431, 51.

Ham, Richard G. et al., Media and Growth Requirements, Meth. Enz., 1979, 44-93, 58.

Hartzell, Stephen W. et al., Mapping of the late promoter of simian virus 40, PNAS USA, 1984, 23-27, 81.

Marchant, Rosalyn J. et al., Metabolic Rates, Growth Phase, and mRNA Levels Influence Cell-Specific Antibody Production Levels from In Vitro-Cultured Mammalian Cells at Sub-Physiological Temperatures, Mol Biotechnol, 2008, 69-77, 39.

Mohammad, Adil et al., An ICP-MS platform for metal content assessment of cell culture media and evaluation of spikes in metal concentration on the quality of an IgG3: [kappa] monoclonal antibody during production, Journal of Pharmaceutical and Biomedical Analysis, 2018, 91-100, 162.

Oguchi, Satoshi et al., pH Condition in temperature shift cultivation enhances cell longevity and specific hMab productivity in CHO culture, Cytotechnology, 2006, 199-207, 52.

Patel, Bhumit et al., Rapid Analytics to Accelerate Process Development and Enable Real-time Release Test, CASSS WCBP, Washington D.C., 2020, 1-27, Slides Jan. 30, 2020.

Pirok, Bob W. J. et al., Recent Developments in Two-Dimensional Liquid Chromatography: Fundamental Improvements for Practical Applications, Anal. Chem., 2018, 240-263, 91.

Ren, Da et al., An improved trypsin digestion method minimizes digestion-induced modifications on proteins, Analytical Biochemistry, 2009, 12-21, 392.

Rogers, Richard S. et al., A View on the Importance of "Multi-Attribute Method" for Measuring Purity of Biopharmaceuticals and Improving Overall Control Strategy, The AAPS Journal, 2018, 1-8, 20:7.

Rogers, Richard S. et al., Development of a quantitative mass spectrometry multi-attribute method for characterization, quality control testing and disposition of biologics, mAbs, 2015, 881-890, 7:5.

USPI, Highlights of Prescribing Information, Merck Sharp & Dohme Corp., 2022, 1-125, N/A.

Xu, Sen et al., Impact of Pluronic F68 on hollow fiber filter-based perfusion culture performance, Bioprocess Biosyst Eng, 2017, 1317-1326, 40.

Design of a Pembrolizumab Manufacturing Plant in Ireland Using Continuous Bioprocess Technology and Single Use Bioreactors.†

\* cited by examiner
† cited by third party

SEQUENCE LISTING

```
<160> NUMBER OF SEQ ID NOS: 15

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Lys Gly Val Ser Thr Ser Gly Tyr Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Ala Ser Tyr Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln His Ser Arg Asp Leu Pro Leu Thr
1               5

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
```

```
                          polypeptide

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys
            100                 105                 110

<210> SEQ ID NO 5
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Tyr Tyr Met Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ile Asn Pro Ser Asn Gly Gly Thr Asn Phe Asn Glu Lys Phe Lys
1               5                   10                  15

Asn

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Asp Tyr Arg Phe Asp Met Gly Phe Asp Tyr
1               5                   10

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120
```

```
<210> SEQ ID NO 10
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

```
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 11
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Pyroglutamate

<400> SEQUENCE: 11

Glu Val Gln Leu Val Gln Ser Gly Val Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Tyr Met Tyr Trp Val Arg Gln Ala Pro Gly Gln Gly Leu Glu Trp Met
            35                  40                  45
Gly Gly Ile Asn Pro Ser Asn Gly Gly Thr Asn Phe Asn Glu Lys Phe
        50                  55                  60
Lys Asn Arg Val Thr Leu Thr Thr Asp Ser Ser Thr Thr Thr Ala Tyr
65                  70                  75                  80
Met Glu Leu Lys Ser Leu Gln Phe Asp Asp Thr Ala Val Tyr Tyr Cys
                85                  90                  95
Ala Arg Arg Asp Tyr Arg Phe Asp Met Gly Phe Asp Tyr Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
```

```
                260                 265                 270
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 12
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Pyroglutamate

<400> SEQUENCE: 12

Glu Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 13
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
```

```
            65                  70                  75                  80
        Met Glu Leu Lys Ser Leu Gln Phe Asp Thr Ala Val Tyr Tyr Cys
                            85                  90                  95

Ala Arg Arg Asp Tyr Arg Phe Asp Met Gly Phe Asp Tyr Trp Gly Gln
                        100                 105                 110

Gly Thr Thr Val Thr Val Ser Ala Ser Thr Lys Gly Pro Ser Val
                    115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                    180                 185                 190

Ser Ser Ser Leu Gly Thr Lys Thr Tyr Thr Cys Asn Val Asp His Lys
                    195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser Gln Glu Asp Pro Glu
                    260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
        305                 310                 315                 320

Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                    340                 345                 350

Pro Ser Gln Glu Glu Met Thr Lys Asn Gln Val Ser Leu Thr Cys Leu
                    355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                    420                 425                 430

His Asn His Tyr Thr Gln Lys Ser Leu Ser Leu Ser Leu Gly
                    435                 440                 445

<210> SEQ ID NO 14
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Pyroglutamate

<400> SEQUENCE: 14
```

| | | | | | | | | | | | | | | |
|---|---|---|---|---|---|---|---|---|---|---|---|---|---|---|
| Glu | Val | Gln | Leu | Val | Gln | Ser | Gly | Val | Glu | Val | Lys | Lys | Pro | Gly | Ala |
| 1 | | | | 5 | | | | | 10 | | | | | 15 |

Ser Val Lys Val Ser Cys Lys Ala Ser Gly Tyr Thr Phe Thr Asn Tyr
                20                     25                     30

Tyr Met Tyr Trp Val Arg Gln Ala Pro Gly Gln Gly Leu Glu Trp Met
        35                     40                    45

Gly Gly Ile Asn Pro Ser Asn Gly Gly Thr Asn Phe Asn Glu Lys Phe
50                       55                     60

Lys Asn Arg Val Thr Leu Thr Thr Asp Ser Ser Thr Thr Thr Ala Tyr
65                   70                  75                     80

Met Glu Leu Lys Ser Leu Gln Phe Asp Thr Ala Val Tyr Tyr Cys
              85                   90                 95

Ala Arg Arg Asp Tyr Arg Phe Asp Met Gly Phe Asp Tyr Trp Gly Gln
            100                 105               110

Gly Thr Thr Val Thr Val Ser Ser Ala Ser Thr Lys Gly Pro Ser Val
       115                   120               125

Phe Pro Leu Ala Pro Cys Ser Arg Ser Thr Ser Glu Ser Thr Ala Ala
130                     135                 140

Leu Gly Cys Leu Val Lys Asp Tyr Phe Pro Glu Pro Val Thr Val Ser
145                     150                 155                 160

Trp Asn Ser Gly Ala Leu Thr Ser Gly Val His Thr Phe Pro Ala Val
              165                 170               175

Leu Gln Ser Ser Gly Leu Tyr Ser Leu Ser Ser Val Val Thr Val Pro
            180                 185               190

Ser Ser Ser Leu Gly Thr Lys Thr Tyr Thr Cys Asn Val Asp His Lys
       195                   200               205

Pro Ser Asn Thr Lys Val Asp Lys Arg Val Glu Ser Lys Tyr Gly Pro
210                     215                 220

Pro Cys Pro Pro Cys Pro Ala Pro Glu Phe Leu Gly Gly Pro Ser Val
225                     230                 235                 240

Phe Leu Phe Pro Pro Lys Pro Lys Asp Thr Leu Met Ile Ser Arg Thr
            245                 250               255

Pro Glu Val Thr Cys Val Val Val Asp Val Ser Gln Glu Asp Pro Glu
            260                 265               270

Val Gln Phe Asn Trp Tyr Val Asp Gly Val Glu Val His Asn Ala Lys
       275                   280               285

Thr Lys Pro Arg Glu Glu Gln Phe Asn Ser Thr Tyr Arg Val Val Ser
290                     295                 300

Val Leu Thr Val Leu His Gln Asp Trp Leu Asn Gly Lys Glu Tyr Lys
305                     310                 315                 320

Cys Lys Val Ser Asn Lys Gly Leu Pro Ser Ser Ile Glu Lys Thr Ile
            325                 330               335

Ser Lys Ala Lys Gly Gln Pro Arg Glu Pro Gln Val Tyr Thr Leu Pro
       340                   345               350

Pro Ser Gln Glu Glu Met Thr Lys Asn Gln Val Ser Leu Thr Cys Leu
            355                 360               365

Val Lys Gly Phe Tyr Pro Ser Asp Ile Ala Val Glu Trp Glu Ser Asn
370                     375                 380

```
Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu
            435                 440                 445

<210> SEQ ID NO 15
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300
```

-continued

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370             375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu
            435                 440                 445
```

COMPOSITIONS OF PROGRAMMED DEATH RECEPTOR 1 (PD-1) ANTIBODIES AND METHODS OF OBTAINING THE COMPOSITIONS THEREOF

FIELD OF THE INVENTION

The invention provides purified compositions of anti-PD-1 antibodies or antigen-binding fragments thereof with less than or equal to about 3.0% oxidation of Met105 in the CDRH3 heavy chain region or about 1.0-12.0% acidic species, and methods of obtaining the purified compositions of the invention.

REFERENCE TO SEQUENCE LISTING SUBMITTED ELECTRONICALLY

The sequence listing of the present application is submitted electronically via EFS-Web as an ASCII formatted sequence listing with a file name 25195-US-NP SEQLIST-20JAN2022.txt, creation date of Jan. 20, 2022, and a size of 30 kb. This sequence listing submitted via EFS-Web is part of the specification and is herein incorporated by reference in its entirety.

BACKGROUND OF THE INVENTION

Immune checkpoint therapies targeting the programmed death receptor-1 (PD-1) axis have resulted in groundbreaking improvements in clinical response in multiple human cancers (Brahmer et al., *N Engl J Med* 2012, 366: 2455-65; Garon et al. *N Engl J Med* 2015, 372: 2018-28; Hamid et al., *N Engl J Med* 2013, 369: 134-44; Robert et al., *Lancet* 2014, 384: 1109-17; Robert et al., *N Engl J Med* 2015, 372: 2521-32; Robert et al., *N Engl J Med* 2015, 372: 320-30; Topalian et al., *N Engl J Med* 2012, 366: 2443-54; Topalian et al., *J Clin Oncol* 2014, 32: 1020-30; Wolchok et al., *N Engl J Med* 2013, 369: 122-33). The interaction of the PD-1 receptor on T-cells with its ligands, PD-L1 and PD-L2, on tumor and immune infiltrating cells regulates T-cell mediated immune responses and may play a role in immune escape by human tumors (Pardoll D M. *Nat Rev Cancer* 2012,12: 252-64). Binding of PD-1 to either of its ligands results in delivery of an inhibitory stimulus to the T cell. Immune therapies targeting the PD-1 axis include monoclonal antibodies directed to the PD-1 receptor (KEYTRUDA™ (pembrolizumab), Merck and Co., Inc., Kenilworth, NJ and OPDIVO™ (nivolumab), Bristol-Myers Squibb, Princeton, NJ) and also those that bind to the PD-L1 ligand (MPDL3280A; TECENTRIQ™ (atezolizumab), Genentech, San Francisco, CA). Both therapeutic approaches have demonstrated anti-tumor effects in numerous cancer types.

Oxidation of methionine is one of the major degradation pathways in many protein pharmaceuticals. Methionine residues in proteins are susceptible to oxidation, resulting in the formation of methionine sulfoxide and, under extreme conditions, sulfones. An exposed methionine residue or a methionine residue in the CDR of an antibody has the potential of impacting the biological activity of the antibody through oxidation. Major degradation pathways of pembrolizumab include oxidation of methionine 105 (Met105) in the heavy chain CDR and Fc methionine residues when exposed to light or peroxide stress. It is desirable to obtain pembrolizumab compositions with low oxidation, in particular at the Met105 position. Deamidation of asparagine residues can lead to succinimide formation, which can then be converted to aspartate or isoaspartate. Deamidation in antibodies, in particular in the CDR regions, has the potential of impacting the biological activity of the antibody. Therefore, it is also desirable to obtain pembrolizumab compositions with low deamidation variants.

SUMMARY OF THE INVENTION

The invention provides compositions of anti-human PD-1 antibodies or antigen-binding fragments thereof with less than or equal to about 3.0% oxidation of Met105 in the CDRH3 heavy chain region. The invention also provides a composition comprising an anti-human PD-1 antibody main species comprising an antibody consisting of two heavy chains and two light chains, each heavy chain consisting of the amino acid sequence of SEQ ID NO: 11, and each light chain consisting of the amino acid sequence of SEQ ID NO: 5, and acidic species of the anti-human PD-1 antibody main species, wherein the amount of acidic species is about 1.0-12.0%. The invention also provides a composition comprising an anti-human PD-1 antibody main species comprising an antibody consisting of two heavy chains and two light chains, each heavy chain consisting of the amino acid sequence of SEQ ID NO: 11, and each light chain consisting of the amino acid sequence of SEQ ID NO: 5, and acidic and basic species of the anti-human PD-1 antibody main species, wherein the amount of main species is about 65-85%. Surprisingly, a continuous perfusion upstream process provided pembrolizumab compositions with lower % Met105 oxidation, lower % acidic species and/or higher % main species compared to pembrolizumab produced by a fed batch process. The invention also provides a method of obtaining the purified compositions by the continuous perfusion process.

Also provided herein are methods of treating cancer in a human patient in need thereof comprising: administering an effective amount of the compositions of the invention to the patient.

DETAILED DESCRIPTION OF THE INVENTION

I. Definitions and Abbreviations

Figure 1:
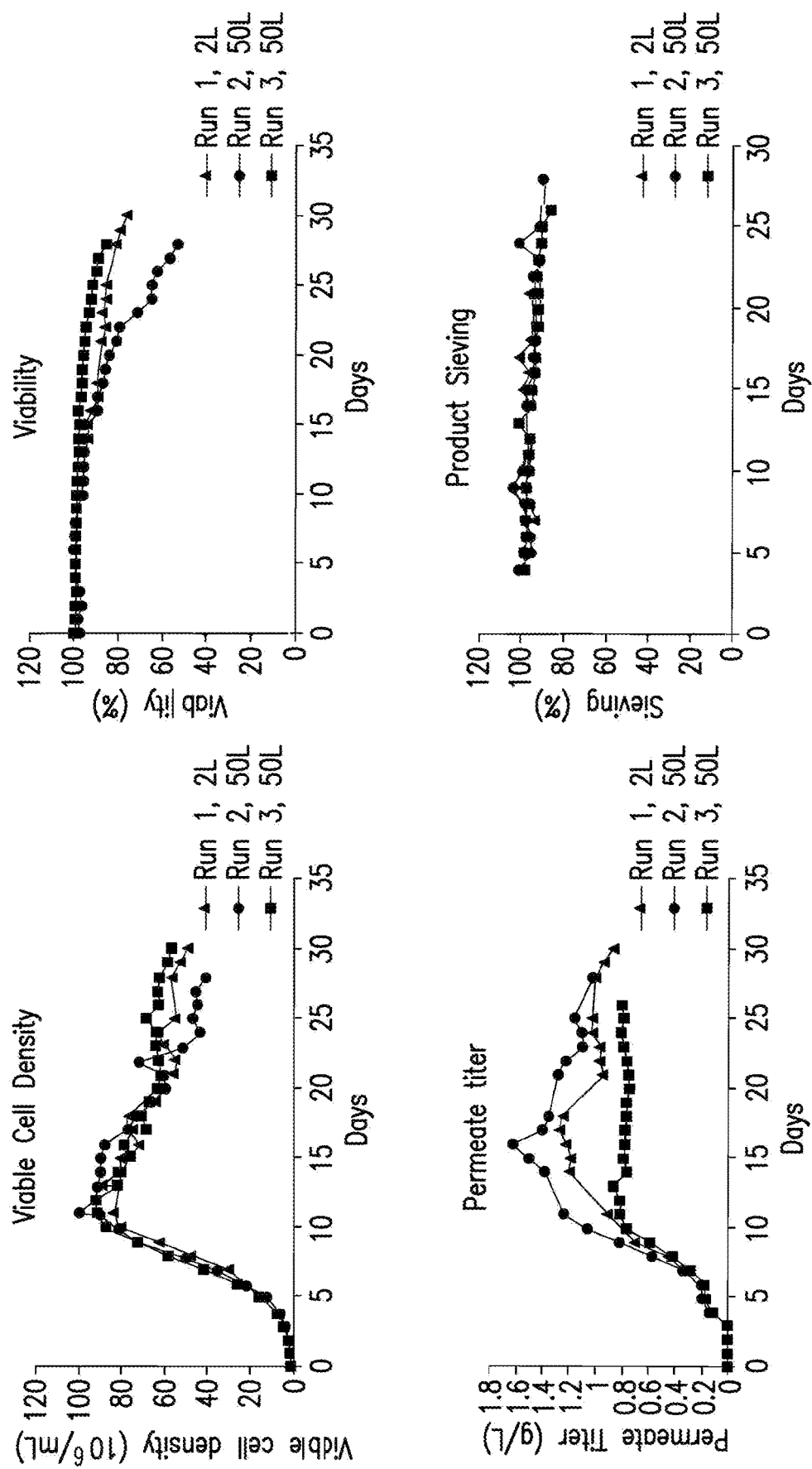
FIG. 1: Cell culture performance of continuous perfusion culture at 2 L and 50 L scales. Top left: Viable Cell Density (VCD); Top right: Viability; Bottom left: permeate titer; and Bottom right: product sieving.

As used throughout the specification and appended claims, the following abbreviations apply:
API active pharmaceutical ingredient
CDR complementarity determining region in the immunoglobulin variable regions
CHO Chinese hamster ovary
CI confidence interval
DS drug substance
EC50 concentration resulting in 50% efficacy or binding
ELISA enzyme-linked immunosorbant assay
FFPE formalin-fixed, paraffin-embedded
FR framework region
HC heavy chain
HNSCC head and neck squamous cell carcinoma
HP-HIC high performance hydrophobic interaction chromatography
HP-IEX high performance ion-exchange chromatography
HP-SEC high performance size exclusion chromatography
IC50 concentration resulting in 50% inhibition
IgG immunoglobulin G
IHC immunohistochemistry or immunohistochemical
mAb monoclonal antibody
NCBI National Center for Biotechnology Information
NSCLC non-small cell lung cancer
PCR polymerase chain reaction
PD-1 programmed death 1 (a.k.a. programmed cell death-1 and programmed death receptor 1)
PD-L1 programmed cell death 1 ligand 1
PD-L2 programmed cell death 1 ligand 2
PS80 or PS-80 polysorbate 80
SWFI sterile water for injection
TNBC triple negative breast cancer
$V_H$ immunoglobulin heavy chain variable region
VK immunoglobulin kappa light chain variable region
$V_L$ immunoglobulin light chain variable region
v/v volume per volume
WFI water for injection
w/v weight per volume So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

As used herein, "acidic species" refers to the anti-PD-1 antibody species that is more acidic (e.g. as determined by cation exchange chromatography) than the anti-PD-1 antibody main species. Such acidic species are detected by various chromatography purification methods for separating molecule variants by charge, such as ion exchange, for example, cation exchange chromatography (e.g. the method described in Example 5) or WCX-10 HPLC (a weak cation exchange chromatography), optionally followed by mass spectroscopy. Generally, the acidic species has a lower isoelectric point (pI) than the main species, and can have a more acidic character due to for example, methionine oxidation, sialylation of asparagine residues or deamidated variants of the antibody, or a combination thereof. Examples of the acidic species include but are not limited to the acidic variants, acidic 1 and pre-main peaks identified in FIG. 6 or 7 of the invention. Any of the acidic species may also have one or more of CHO N-linked glycans selected from the group consisting of G0-F, G1-F, G2-F, G0, G1, G2 and Man5, for example at N297 in the CH2 domain.

In one embodiment, the anti-PD-1 antibody acidic species is as identified by peak(s) eluted prior to the main peak according to a cation ion exchange method. In another embodiment, the anti-PD-1 antibody acidic species is as identified by peak(s) eluted prior to the main peak according to a weak cation ion exchange method. In an ion exchange chromatography method, the "% acidic species" refers to the total area of acidic species peaks divided by the total area of all peaks in the elution chromatogram.

As used herein, "acidic1 species" refers to an acidic species with the presence of one or more of deamidation, succinimide, aspartate or isoaspartate formation in one or more of N384, N389 and N390 of the heavy chain of the anti-PD-1 antibody main species. Such acidic1 species are detected by various chromatography purification methods for separating molecule variants by charge, such as ion exchange, for example, cation exchange chromatography (e.g. the method described in Example 5) or WCX-10 HPLC (a weak cation exchange chromatography), followed by mass spectroscopy of the acidic species peaks.

Figure 6:
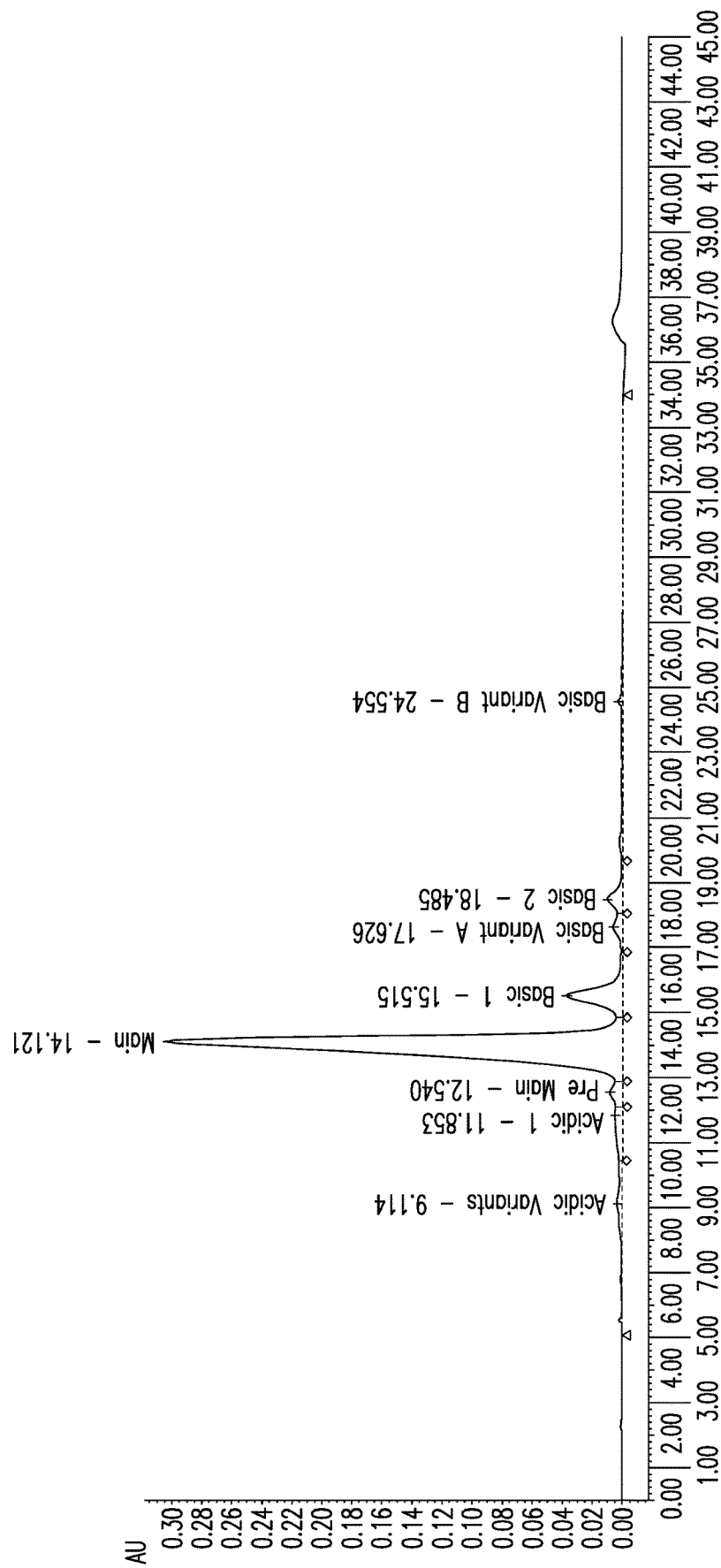
FIG. 6: Ion exchange chromatography analytical diagram of pembrolizumab after Protein A chromatography purification of HCCF from the continuous perfusion process. The retention time of each peak is annotated in the figure.
Figure 7:
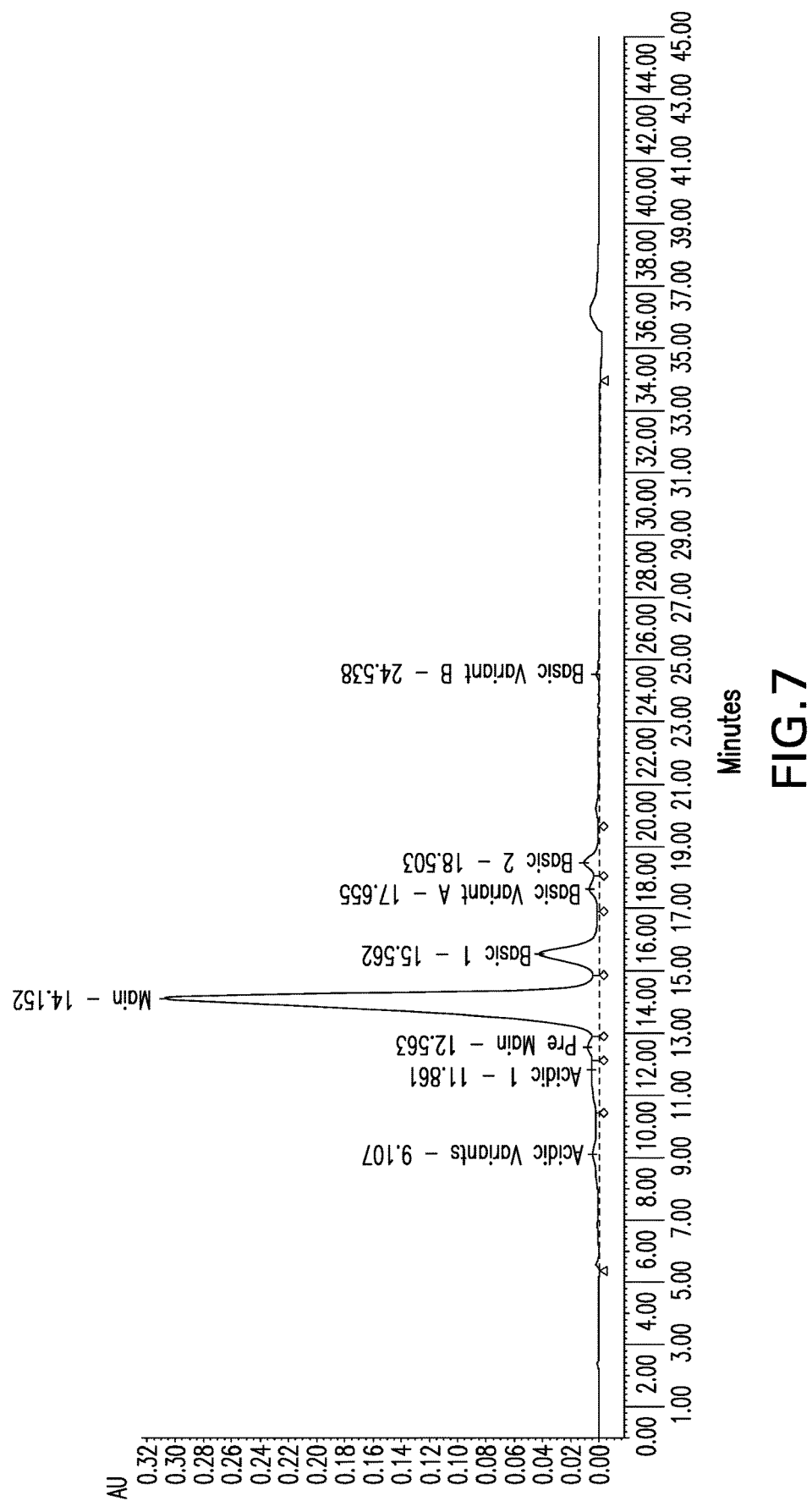
FIG. 7: Ion exchange chromatography analytical diagram of pembrolizumab after Anion exchange chromatography and Protein A chromatography purification of HCCF from the continuous perfusion process. The retention time of each peak is annotated in the figure.

In one embodiment, the anti-PD-1 antibody acidic1 species is as identified in acidic 1 peak of FIG. 6 or 7, and eluted according to the cation ion exchange method described in Example 5. In an ion exchange chromatography method, the "% acidic1 species" refers to the total area of acidic1 peak divided by the total area of all peaks in the elution chromatogram.

As used herein, "acidic variants species" refers to an acidic species with the presence of one or more of deamidation, succinimide, aspartate or isoaspartate formation in one or more of N31, N52, N55, N59, and N61 of the heavy chain; or the presence of M105 oxidation in the heavy chain; or a combination thereof of the anti-PD-1 antibody main species. Such acidic variants species are detected by various chromatography purification methods for separating molecule variants by charge, such as ion exchange, for example, cation exchange chromatography (e.g. the method described in Example 5) or WCX-10 HPLC (a weak cation exchange chromatography), followed by mass spectroscopy of the acidic species peaks.

In one embodiment, the anti-PD-1 antibody acidic variants species is the anti-PD-1 antibody species as identified by the acidic variants peak(s) in FIG. 6 or 7, and eluted according to the cation ion exchange method described in Example 5. In an ion exchange chromatography method, the "% acidic variants species" refers to the total area of acidic variants peak(s) divided by the total area of all peaks in the elution chromatogram.

As used herein, "basic species" refers to the anti-PD-1 antibody species that is more basic (e.g. as determined by cation exchange chromatography) than the anti-PD-1 antibody main species. Such basic species are detected by various chromatography purification methods for separating molecule variants by charge, such as ion exchange, for example, cation exchange chromatography (e.g. the method described in Example 5) or WCX-10 HPLC (a weak cation exchange chromatography), optionally followed by mass spectroscopy. Generally, the basic species has a higher pI than the main species, and can have a more basic character due to modifications or differences from the main species including but not limited to the presence of the C-terminal lysine residue (SEQ ID NO:10 or 12), the presence of N-terminal glutamine residue (SEQ ID NO: 10 or 13), or alpha-amidation of a C-terminal leucine residue (SEQ ID NO: 14 or 15), truncation of N-terminal amino acid residues in one or both heavy chains according to the amino acid sequence in any one of SEQ ID NO: 10-15, or a combination thereof. Examples of the basic species include but are not limited to the basic variant A, basic variant B, basic 1 and basic 2 peaks identified in FIG. 6 or 7 of the invention. Any of the basic species may also have one or more of CHO N-linked glycans selected from the group consisting of G0-F, G1-F, G2-F, G0, G1, G2 and Man5, for example at N297 in the CH2 domain.

In one embodiment, the anti-PD-1 antibody basic species is as identified by peak(s) eluted after the main peak according to a cation ion exchange method. In another embodiment, the anti-PD-1 antibody basic species is as identified by peak(s) eluted after the main peak according to a weak cation ion exchange method. In an ion exchange chromatography method, the "% basic species" refers to the total area of basic species peak(s) divided by the total area of all peaks in the elution chromatogram.

As used herein, "main species" refers to the anti-PD-1 antibody species identified as the majority of the antibody species in a mixture with one or more acidic or basic species thereof. Such main species are detected by various chromatography purification methods for separating molecule variants by charge, such as ion exchange, for example, cation exchange chromatography (e.g. the method described in Example 5) or WCX-10 HPLC (a weak cation exchange chromatography), optionally followed by mass spectroscopy. The mixture can be a result of for example, antibody preparations from mammalian cells and post-translational modifications thereof, upstream and downstream processing, or storage. The main species may also have one or more of CHO N-linked glycans selected from the group consisting of G0-F, G1-F, G2-F, G0, G1, G2 and Man5, for example at N297 in the CH2 domain.

In one embodiment, the main species comprises the anti-PD-1 antibody consisting of two heavy chains and two light chains, each heavy chain consisting of the amino acid sequence of SEQ ID NO: 11, and each light chain consisting of the amino acid sequence of SEQ ID NO: 5. In another embodiment, the anti-PD-1 antibody main species is produced from a Chinese Ovary cell that comprises a polynucleotide encoding a light chain that consists of the amino acid sequence of SEQ ID NO: 5 and a polynucleotide encoding a heavy chain that consists of the amino acid sequence of SEQ ID NO: 10, 13 or 15, or a polynucleotide encoding the light chain and the heavy chain.

In one embodiment, the main species is identified as the main peak according to a cation ion exchange method. In an ion exchange method, the "% main species" refers to the total area of main peak divided by the total area of all peaks in the elution chromatogram.

As used herein, "basic 1 species" refers to a basic species consisting of two heavy chains and two light chains, one heavy chain consisting of the amino acid sequence of SEQ ID NO: 11, one heavy chain consisting of the amino acid sequence of SEQ ID NO: 12, and each light chain consisting of the amino acid sequence of SEQ ID NO: 5; or a basic species consisting of two heavy chains and two light chains, one heavy chain consisting of the amino acid sequence of SEQ ID NO: 11, one heavy chain consisting of the amino acid sequence of SEQ ID NO: 14, wherein the C-terminal leucine is alpha-amidated, and each light chain consisting of the amino acid sequence of SEQ ID NO: 5; or a combination thereof. Such basic 1 species are detected by various chromatography purification methods for separating molecule variants by charge, such as ion exchange, for example, cation exchange chromatography (e.g. the method described in Example 5) or WCX-10 HPLC (a weak cation exchange chromatography), followed by mass spectroscopy of the basic species peaks.

In one embodiment, the anti-PD-1 antibody basic 1 species is as identified by basic 1 peak in FIG. 6 or 7, and eluted according to the cation ion exchange method described in Example 5. In an ion exchange chromatography method, the "% basic1 species" refers to the total area of basic1 peak divided by the total area of all peaks in the elution chromatogram.

As used herein, "deamidated variant" refers to an antibody wherein one or more asparagine residue(s) have been deamidated. The deamidated variant can be in the form of succinimide, aspartate or isoaspartate. i.e., the neutral amide side chain has been converted to a residue with an overall acidic character.

In one aspect of measuring the main species, acidic species or basic species, a Thermo Scientific ProPac WCX-10 column is used for the cation ion exchange method. In another embodiment, a Thermo Scientific ProPac WCX-10 column is used, with a Mobile Phase (A) 24 mM MES pH 6.1 with 4% acetonitrile, and mobile phase (B) 20 mM sodium phosphate, 95 mM NaCl pH 8.0 with 4% acetonitrile, and a column temperature of 35° C. In one embodiment, a non-linear gradient is used with: 22%-22% B for 0-0.6 min; 22%-29% B for 0.6-15.0 min; 29%-70% B for 15.0-30.0 min; 70%-100% B for 30.0-30.5 min; and 100%-100% B from 30.5-33.0 min. In a further embodiment, the cation ion exchange method is described in Example 5.

As used herein, "express" and "expression" refer to allowing or causing the information in a gene or coding sequence, e.g., an RNA or DNA, to become manifest; for example, producing a protein by activating the cellular functions involved in transcription and translation of a corresponding gene. A DNA sequence can be expressed in or by a cell to form an "expression product" such as an RNA (e.g., mRNA) or a protein. The expression product itself may also be said to be "expressed" by the cell.

As used herein, "expression vector" or "expression construct" refer to a vehicle (e.g., a plasmid) by which a polynucleotide comprising regulatory sequences operably linked to a coding sequence can be introduced into a host cell where the coding sequence is expressed using the transcription and translation machinery of the host cell.

"Expression cassette" as used herein, refers to a polynucleotide that comprises elements sufficient to control expression of a gene, including but not limited to, a promoter operably linked to the gene sequence or operably linked to a multiple cloning site for inserting the gene sequence, and a polyA signal. In some embodiments, the expression cassette further comprises one or more regulatory elements that can regulate the expression of the gene at transcriptional, translational, and/or chromatin levels.

As used herein, "promoter" or "promoter sequence" refer to a segment of DNA that contains a regulatory region capable of recruiting an RNA polymerase (e.g., directly or through other promoter-bound proteins or substances) and initiating transcription of a coding sequence. Within the promoter sequence may be found a transcription initiation site (conveniently defined, for example, by mapping with nuclease 51), as well as protein binding domains (consensus sequences) responsible for the recruiting of RNA polymerase.

As used herein, "enhancer" or "enhancer sequence" refer to a DNA regulatory region that enhances transcription of a promoter independently of its distance, location, or orientation to the promoter. In certain embodiments, the enhancer is immediately adjacent to the promoter. In some embodiments, the enhancer is distant from the promoter. In other embodiments, the promoter and the enhancer are one combined sequence, referred as a "combo enhancer/promoter" herein.

As used herein, "internal ribosome entry site" or "IRES" refer to an RNA element or sequence that allows for translation initiation in a cap-independent manner by recruiting ribosomes directly. As used herein, the term "internal ribosome entry site" or "IRES" also encompasses the DNA sequence that can be transcribed into the RNA sequence that allows for translation initiation in a cap-independent manner by recruiting ribosomes directly. IRES can be a wild type IRES from any species or a variant or mutant thereof, whether naturally occurred or man-made. Examples of IRES that can be used include, but are not limited to, the nucleotide sequence of the 5' nontranslated region of encephalomyocarditis virus (EMCV) (GenBank: M81861.1; Duke et al., Sequence and structural elements that contribute to efficient encephalomyocarditis virus RNA translation. J Virol. 1992 March; 66(3):1602-9.), IRES element described by Bochkov & Palmenberg (Translational efficiency of EMCV IRES in bicistronic vectors is dependent upon IRES sequence and gene location. Biotechniques. 2006 September; 41(3):283-4), IRES element from expression vector pInSRT-GFP (GenBank LC417349.1), IRES element from expression vector pCeMM-CTAP(SG) (GenBank EF467048.1), IRES element described by Jang & Wimmer (Cap-independent translation of encephalomyocarditis virus RNA: structural elements of the internal ribosomal entry site and involvement of a cellular 57-kD RNA-binding protein. Genes Dev. 1990 September; 4(9):1560-72), IRES element from expression vector pIRESneo3 (Clontech/Takara Bio), IRES elements described in WO 2015/016786, WO 2015/021077, WO 2016/003368, WO 2016/074016, or WO 2013/092743, or variants thereof.

As used herein, "regulatory element," "regulatory region," or "regulatory sequence" refer to a polynucleotide sequence that has the ability to regulate (such as, initiate, activate, enhance, increase, decrease, inhibit, suppress, or silence) expression of a gene. In some embodiments, the regulation is achieved by binding of cellular factors to the polynucleotide sequence. In other embodiments, the regulation is achieved by interaction between cellular factors. The regulation can occur at one or more different levels in the expression process from DNA to protein, including but not limited to transcriptional, translational, or chromatin levels.

As used herein, "insulator" refers to a class of DNA elements or sequences that possess an ability to isolate the proximal DNA region by preventing the positional effect from the surrounding chromosome area. In certain embodiments, the insulator can block enhancer when the insulator is situated between the enhancer and the promoter. In some embodiments, the insulator can act as barriers that prevent the advance of nearby condensed chromatin that might otherwise silence expression. In other embodiments, the insulator can block enhancer and act as barriers.

As used herein, "expression augmenting sequence element" or "EASE", refer to a DNA element or sequence that can increase expression of a protein when the DNA element or sequence is placed upstream of the promoter that controls the expression of the protein.

As used herein, "tripartite leader" or "TPL" refer to an RNA element or sequence in the 5'-untranslated region of adenovirus late-expressed mRNA that has an ability to initiate translation of the late-expressed mRNA in a cap-independent manner. As used herein, the term "tripartite leader" or "TPL" also encompasses the DNA sequence that can be transcribed into the RNA sequence in the 5'-untranslated region of adenovirus late-expressed mRNA that has an ability to initiate translation of the late-expressed mRNA in a cap-independent manner.

As used herein, "inverted terminal repeat" or "ITR", in the context of transposon technology, refers to a DNA element or sequence and its inverted version at either end of a transposon that signals where the breakage and joining should occur.

As used herein, "selectable marker" or "selection marker" refer to a protein which allows the specific selection of cells that express this protein by the addition of a corresponding selecting agent to the culture medium. In certain embodiments, the selectable marker is a eukaryotic selectable marker, which allows selection of eukaryotic cells that express the marker protein. In some embodiments, the selectable marker is a bacterial selectable marker, which allows selection of bacterial cells that express the marker protein.

A "polynucleotide sequence", "nucleic acid sequence" or "nucleotide sequence", as used herein, refer to a series of nucleotide bases (also called "nucleotides") in a nucleic acid, such as DNA or RNA, and means any chain of two or more nucleotides.

As used herein, a "host cell" refers to any cell of any organism that is used for the purpose of producing a recombinant protein encoded by an expression vector or propagating the expression vector introduced into the host cell. A "mammalian recombinant host cell" refers to a mammalian host cell that comprises a heterologous expression vector, which may or may not be integrated into the host cell chromosome. A "bacterial recombinant host cell" refers to a bacterial host cell that comprises a heterologous expression vector, which may or may not be integrated into the host cell chromosome.

The term "fed-batch culture", as used herein, refers to a method of culturing cells in which additional nutrients are provided to the culture during the cultivation process. A fed-batch culture is typically stopped at some point and the cells and/or components in the medium are harvested. The product accumulates and remains in the bioreactor until the end of the run.

As used herein, "harvesting" an antibody or antigen-binding fragment involves separating it from particulate matter that can include host cells, cell aggregates, and/or lysed cell fragments, into a cell-free fraction that is substantially free of host cells and cellular debris, i.e., a cell-free "permeate." Such cells and cellular debris is removed from the cell culture broth, for example, by centrifugation, depth filtration and/or microfiltration. For example, to make the cell-free permeate, one can employ hollow fiber membranes or a series of filtration steps such as depth filtration. "Continuously harvesting" refers to harvesting cell culture broth while antibody production takes place in the bioreactor. Secreted protein products in the bioreactor can be continuously harvested from the cell culture broth by microfiltration during the process of removing medium via the perfusion system, the protein of interest thus being isolated in a microfilter permeate exiting the perfusion system. The microfilter can be a Tangential Flow Filtration (TFF) unit including a hollow fiber module or Alternating Tangential Flow Filtration (ATF) unit. Commercially available TFF units include, but are not limited to, Microza® TFF unit or KrosFlow®Max. Commercially available hollow fiber modules can be obtained for example, from Pall or Repligen. In one embodiment, the perfusion bioreactor has a constant permeate rate for the cell culture broth comprising the antibody or antigen-binding fragment to maintain a consistent flow rate to the affinity chromatography step.

As used herein, "cell culture broth" refers to broth comprising the host cells, cellular debris, cell culture medium, antibody or antigen-binding fragment during the cell growth and antibody production process.

As used herein, "harvest cell culture fluid" or "HCCF" refers to the cell culture fluid comprising the antibody or antigen-binding fragment obtained after harvesting the cell culture broth, which is substantially free of host cells and cellular debris. In one embodiment, the HCCF is a cell-free permeate.

As used herein, "fluidly connected," "fluidly," or is "fluidly connected to", or "fluidly receives material from", refers to another step of the manufacturing process or from another system, when material containing the protein of interest flows by pipe, tubing, or other closed conduit between steps or systems without manual loading or unloading.

As used herein in the context of HCCF, "continuously purifying" refers to uninterrupted flow of the HCCF to at least one affinity stationary phase for at least the loading step, and optionally an uninterrupted flow for any washing or elution steps.

As used herein, "perfusion" or "perfusing" refer to a method of culturing cells in which additional fresh medium is provided continuously over some period of time, to the culture (subsequent to the beginning of the culture process), and simultaneously removing medium while harvesting the antibody or antigen-binding fragment from the medium continuously. The fresh medium typically provides nutritional supplements for the cells that have been depleted during the culturing process.

"Perfusion rate", as used herein, refers to the rate at which fresh medium is provided and cell culture fluid is removed.

As used herein, a "perfusion bioreactor" refers to a bioreactor for culturing cells in which equivalent volumes of culture medium can be added to and concurrently removed from the reactor. In one embodiment, the cells are retained in the bioreactor. A perfusion bioreactor includes a bioreactor and an operably attached perfusion system, which provides a steady source of fresh nutrient medium and removal of cell waste products. The bioreactor and the perfusion system of the perfusion bioreactor can be separate mechanical units that operate in coordination. Numerous commercially available examples include, but are not limited to, a variety of Xcellerex® brand single-use bioreactors (SUBs; GE Healthcare Life Sciences) and KrosFlo® brand perfusion flow-path assemblies and systems (Spectrum; Repligen), which bioreactors and perfusion systems can be suitably combined into a perfusion bioreactor by the skilled practitioner. Alternatively, the bioreactor and the perfusion system can be assembled into a single mechanical unit, for example, but not limited to, a 3D Biotek brand perfusion bioreactor (Sigma-Aldrich).

The term "surge vessel", as used herein, refers to a well-mixed (providing sufficient mixing such that fluid is homogenous) storage reservoir, mixing vessel, feed tank, or collection vessel (or interchangeably, a "collection tank"), at the downstream end of a conduit, feeder, dam, pipe, or tubing, to absorb discrepant flow rates between two fluidly connected unit operations, e.g., the flow rate of a permeate coming from a bioreactor and the flow rate of a first chromatography system under automated control in continuous or semi-continuous format process embodiments of the invention. The surge vessel absorbs changes or differences in flow rates by allowing the volume to surge within pre-set volume range limits between the fluidly connected unit operations.

The term "residence time", as used herein, refers to the average time a fluid solution spends inside a vessel. For perfusion this is the inverse of the exchange rate (e.g. 2VVD has a mean residence time of 0.5 day). Sieving of solution components, retention of solution components by the membrane is neglected for residence time.

As used herein, "M105", "Met105", or "Methionine105" refers to the methionine in CDRH3 region of the heavy chain in SEQ ID NO: 8 (RDYRFDMGFDY).

As used herein, "% oxidation of M105" or "% oxidation of Met105" refer to a) total amount of anti-PD-1 antibody fragment(s) of the invention with oxidized Met105 versus total amount of anti-PD-1 antibody fragment(s) of the invention with and without oxidized Met105; orb) total amount of anti-PD-1 antibody of the invention with oxidized Met105 versus total amount of anti-PD-1 antibody of the invention with and without oxidized Met105. Calculation method a) can be used according to the reduced peptide mapping method provided in the Examples. Calculation method b) can be used for example, in a Hydrophobic Interaction Chromatography (HIC) or Reverse Phase HPLC method as described in WO2018/204368, incorporated by reference in its entirety.

By "binding" an antibody or antigen-binding fragment to a stationary phase, is meant exposing the antibody or antigen-binding fragment to the stationary phase under appropriate conditions (pH and/or conductivity) such that the antibody or antigen-binding fragment is reversibly associated with the stationary phase by interactions between the antibody or antigen-binding fragment and the ligand immobilized on the stationary phase.

As used herein, the term "equilibration solution" refers to a solution used to equilibrate the stationary phase prior to loading the antibody or antigen-binding fragment on the stationary phase. The equilibration solution can comprise one or more of a salt and buffering species. In one embodiment, the equilibration solution is the same condition as the loading solution comprising the antibody or antigen-binding fragment.

As used herein, the term "loading solution" refers to the solution which is used to load the composition comprising the antibody or antigen-binding fragment of interest and one or more impurities onto the stationary phase. The loading solution may optionally further comprise one or more of a buffering species, and salt.

As used herein, the term "wash solution" refers to a solution used to wash or re-equilibrate the stationary phase, prior to eluting the antibody or antigen-binding fragment of interest. For washing, the conductivity and/or pH of the wash solution is/are such that the impurities are removed from the stationary phase. For re-equilibration, the wash solution and equilibration solution may be the same, but this is not required. The wash solution can comprise one or more of a salt and buffering species.

As used herein, the "elution solution" refers to the solution used to elute the antibody or antigen-binding fragment of interest from the stationary phase. The elution solution can comprise one or more of a salt, or buffering species. The presence of one or more of salt, buffering species, pH or conductivity of the elution solution is/are such that the antibody or antigen-binding fragment is eluted from the stationary phase.

As used herein, the term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is mS/cm, and can be measured using a conductivity meter sold, e.g., within the GE Healthcare Akta™ System. The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Examples below.

As used herein, "purifying" an antibody or antigen-binding fragment of interest or "purified composition" refers to increasing the degree of purity of the antibody or antigen-binding fragment in the composition by removing (completely or partially) at least one impurity from the composition. The impurity can be host cell components such as serum, proteins or nucleic acids, cellular debris, growth medium or antibody aggregates. The term is not intended to refer to a complete absence of such biological molecules or to an absence of water, buffers, or salts or to components of a pharmaceutical composition that includes the antibody or antigen-binding fragment.

As used herein, "continuous multi-column chromatography system" refers to a chromatography system containing at least two stationary phases with similar impurity separation function, which allow at least one stationary phase to load the sample, and at least one stationary phase to perform the non-loading steps (one or more of equilibration, washing, elution and regeneration).

As used herein, "stationary phase" refers to any surface onto which one or more ligands can be immobilized. The stationary phase may be a suspension, a discontinuous phase of discrete particles, plate, sensor, chip, capsule, cartridge, resin, beads, monolith, gel, a membrane, or membrane adsorber etc. Stationary phases may also be packed into a purification column (e.g. packed with resin beads). Examples of materials for forming the stationary phase include mechanically stable matrices such as porous or non-porous beads, inorganic materials (e.g., porous silica, controlled pore glass (CPG) and hydroxyapatite), synthetic organic polymers (e.g., polyacrylamide, polymethylmethacrylate, polystyrene-divinylbenzene, poly(styrenedivinyl)benzene, polyacrylamide, ceramic particles and derivatives of any of the above) and polysaccharides (e.g., cellulose, agarose and dextran). See Jansson, J. C.; Rydén, L. *Protein Purification*; Wiley: New York, 1998.

As used herein, "impurity" refers to a material different from the desired antibody or antigen-binding fragment. The impurity can be Host Cell Protein (HCP), Host Cell DNA (HC-DNA), protein aggregates or clips and other undesired protein modifications (i.e., oxidized species, acid variant species).

"Treat" or "treating" a cancer, as used herein, refers to the administration of a composition of the invention to a subject having an immune condition or cancerous condition, or diagnosed with a cancer or pathogenic infection (e.g. viral, bacterial, fungal), to achieve at least one positive therapeutic effect, such as for example, reduced number of cancer cells, reduced tumor size, reduced rate of cancer cell infiltration into peripheral organs, or reduced rate of tumor metastasis or tumor growth. "Treatment" may include one or more of the following: inducing/increasing an antitumor immune response, stimulating an immune response to a pathogen, toxin, and/or self-antigen, stimulating an immune response to a viral infection, decreasing the number of one or more tumor markers, halting or delaying the growth of a tumor or blood cancer or progression of disease associated with PD-1 binding to its ligands PD-L1 and/or PD-L2 ("PD-1-related disease") such as cancer, stabilization of PD-1-related disease, inhibiting the growth or survival of tumor cells, eliminating or reducing the size of one or more cancerous lesions or tumors, decreasing the level of one or more tumor markers, ameliorating, abrogating the clinical manifestations of PD-1-related disease, reducing the severity or duration of the clinical symptoms of PD-1-related disease such as cancer, prolonging the survival of a patient relative to the expected survival in a similar untreated patient, inducing complete or partial remission of a cancerous condition or other PD-1 related disease.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

Positive therapeutic effects in cancer can be measured in a number of ways (See, W. A. Weber, *J Nucl. Med.* 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by administration of a composition of the invention is any of progression free survival (PFS), disease free survival (DFS) or overall survival (OS). PFS, also referred to as "Time to Tumor Progression" indicates the length of time during and after treatment that the cancer does not grow, and includes the amount of time patients have experienced a complete response or a partial response, as well as the amount of time patients have experienced stable disease. DFS refers to the length of time during and after treatment that the patient remains free of disease. OS refers to a prolongation in life expectancy as compared to naive or untreated individuals or patients. While an embodiment of the compositions, treatment methods, and uses of the invention may not be effective in achieving a positive therapeutic effect in every patient, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

As used herein, the term "patient" (alternatively referred to as "subject" or "individual" herein) refers to a mammal (e.g., rat, mouse, dog, cat, rabbit) capable of being treated with the compositions or compositions of the invention, most preferably a human. In some embodiments, the patient is an adult patient. In other embodiments, the patient is a pediatric patient. Those "in need of treatment" include those patients that may benefit from treatment with the compositions or compositions of the invention, e.g. a patient suffering from cancer or an immune condition.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, humanized, fully human antibodies, and chimeric antibodies.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The variable regions of each light/heavy chain pair form the antibody binding site. Thus, in general, an intact antibody has two binding sites. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) *Adv. Prot. Chem.* 32:1-75; Kabat, et al., (1977) *J Biol. Chem.* 252: 6609-6616; Chothia, et al., (1987) *J Mol. Biol.* 196:901-917 or Chothia, et al., (1989) *Nature* 342:878-883.

As used herein, the term "pharmaceutically effective amount" or "effective amount" refers to an amount whereby sufficient therapeutic composition or composition is introduced to a patient to treat a diseased or condition. One skilled in the art recognizes that this level may vary according the patient's characteristics such as age, weight, etc.

The term "about", when modifying the quantity (e.g., mM, or M) of a substance or composition, the percentage (v/v or w/v) of a composition component, the pH of a solution/composition, or the value of a parameter characterizing a step in a method, or the like refers to variation in the numerical quantity that can occur, for example, through typical measuring, handling and sampling procedures involved in the preparation, characterization and/or use of the substance or composition; through instrumental error in these procedures; through differences in the manufacture, source, or purity of the ingredients employed to make or use the compositions or carry out the procedures; and the like. In certain embodiments, "about" can mean a variation of =0.1%, 0.5%, 1%, 2%, 3%, 4%, 5%, or 10% of the value.

The terms "cancer", "cancerous", or "malignant", as used herein, refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer.

As used herein, the terms "PD-1 binding fragment," "antigen binding fragment thereof," "binding fragment thereof" or "fragment thereof," encompass a fragment or a derivative of an antibody that still substantially retains its biological activity of binding to antigen (human PD-1) and inhibiting its activity (e.g., blocking the binding of PD-1 to PDL1 and PDL2). Therefore, the term "antibody fragment"

or PD-1 binding fragment refers to a portion of a full length antibody, generally the antigen binding or variable region thereof. Examples of antibody fragments include Fab, Fab', F(ab')$_2$, and Fv fragments. Typically, a binding fragment or derivative retains at least 10% of its PD-1 inhibitory activity. In some embodiments, a binding fragment or derivative retains at least 25%, 50%, 60%, 70%, 80%, 90%, 95%, 99% or 100% (or more) of its PD-1 inhibitory activity, although any binding fragment with sufficient affinity to exert the desired biological effect will be useful. In some embodiments, an antigen binding fragment binds to its antigen with an affinity that is at least two fold greater, preferably at least ten times greater, more preferably at least 20-times greater, and most preferably at least 100-times greater than the affinity with unrelated antigens. In one embodiment the antibody has an affinity that is greater than about $10^9$ liters/mol, as determined, e.g., by Scatchard analysis. Munsen et al. (1980) *Analyt. Biochem.* 107:220-239. It is also intended that a PD-1 binding fragment can include variants having conservative amino acid substitutions that do not substantially alter its biological activity.

"Humanized antibody," as used herein, refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will generally comprise the same CDR sequences of the parental rodent antibodies, although certain amino acid substitutions may be included to increase affinity, increase stability of the humanized antibody, or for other reasons.

The antibodies of the invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

"Conservatively modified variants" or "conservative substitution," as used herein, refers to substitutions of amino acids that are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

In addition, those of skill in this art recognize that, in general, single amino acid substitutions in non-essential regions of a polypeptide do not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Tumor Proportion Score (TPS)" refers to the percentage of tumor cells expressing PD-L1 on the cell membrane at any intensity (weak, moderate or strong). Linear partial or complete cell membrane staining is interpreted as positive for PD-L1.

"Mononuclear inflammatory density score (MIDS)" refers to the ratio of the number of PD-L1 expressing mononuclear inflammatory cells (MIC) infiltrating or adjacent to the tumor (small and large lymphocytes, monocytes, and macrophages within the tumor nests and the adjacent supporting stroma) compared to the total number of tumor cells. The MIDS is recorded at a scale from 0 to 4 with 0=none; 1=present, but less than one MIC for every 100 tumor cells (<1%); 2=at least one MIC for every 100 tumor cells, but less than one MIC per 10 tumor cells (1-9%); 3=at least one MIC for every 10 tumor cells, but fewer MIC's than tumor cells (10-99%); 4=at least as many MIC's as tumor cells (≥100%).

"Combined positive score (CPS)" refers to the ratio of the number of PD-L1 positive tumor cells and PD-L1 positive mononuclear inflammatory cells (MIC) within the tumor nests and the adjacent supporting stroma (numerator) compared to the total number of tumor cells (denominator; i.e., the number of PD-L1 positive and PD-L1 negative tumor cells). PD-L1 expression at any intensity is considered positive, i.e., weak (1+), moderate (2+), or strong (3+).

"PD-L1 expression positive" refers to a Tumor Proportion Score, Mononuclear Inflammatory Density Score or Combined Positive Score of at least 1%; AIS is ≥5; or elevated level of PD-L1 expression (protein and/or mRNA) by malignant cells and/or by infiltrating immune cells within a tumor compared to an appropriate control.

"Microsatellite instability (MSI)" refers to the form of genomic instability associated with defective DNA mismatch repair in tumors. See Boland et al., *Cancer Research* 58, 5258-5257, 1998. In one embodiment, MSI analysis can be carried out using the five National Cancer Institute (NCI) recommended microsatellite markers: BAT25 (GenBank accession no. 9834508), BAT26 (GenBank accession no. 9834505), D5S346 (GenBank accession no. 181171), D2S123 (GenBank accession no. 187953), D17S250 (GenBank accession no. 177030). Additional markers for example, BAT40, BAT34C4, TGF-β-RII and ACTC can be used. Commercially available kits for MSI analysis include, for example, the Promega MSI multiplex PCR assay, FoundationOne® CDx (F1CDx) next generation sequencing based in vitro diagnostic device using DNA isolated from formalin-fixed, paraffin-embedded (FFPE) tumor tissue specimens.

"High frequency microsatellite instability" or "microsatellite instability-high (MSI-H)" refers to if two or more of the five NCI markers indicated above show instability or ≥30-40% of the total markers demonstrate instability (i.e. have insertion/deletion mutations).

"Non-MSI-H cancer" as used herein refers to microsatellite stable (MSS) and low frequency MSI (MSI-L) cancer.

"Microsatellite Stable (MSS)" refers to if none of the five NCI markers indicated above show instability (i.e. have insertion/deletion mutations).

"Proficient mismatch repair (pMMR) cancer" refers to normal expression of MMR proteins (MLH1, PMS2, MSH2, and MSH6) in tumor specimen by IHC. Commercially available kits for MMR analysis include the Ventana MMR IHC assay.

"Mismatch repair deficient (dMMR) cancer" refers to low expression of one or more MMR protein(s) (MLH1, PMS2, MSH2, and MSH6) in a tumor specimen by IHC.

"Variable regions" or "V region" as used herein means the segment of IgG chains which is variable in sequence between different antibodies. It extends to Kabat residue 109 in the light chain and 113 in the heavy chain.

The term "buffer" encompasses those agents which maintain the solution pH of the compositions of the invention in an acceptable range.

The term "pharmaceutical composition" refers to preparations with pharmaceutically acceptable excipients which are in such form as to permit the active ingredients to be effective, and which contains no additional components which are toxic to the subjects to which the composition would be administered.

"Pharmaceutically acceptable" refers to excipients (vehicles, additives) and compositions that can reasonably be administered to a subject to provide an effective dose of the active ingredient employed and that are "generally regarded as safe" e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

"Pembrolizumab" (formerly known as MK-3475, SCH 900475 and lambrolizumab) alternatively referred to herein as "pembro," is a humanized IgG4 mAb with the structure described in *WHO Drug Information*, Vol. 27, No. 2, pages 161-162 (2013) and which comprises the heavy and light chain amino acid sequences and CDRs described in Table 2. Pembrolizumab has been approved by the U.S. FDA as described in the Prescribing Information for KEYTRUDA™ (Merck & Co., Inc., Whitehouse Station, NJ USA; initial U.S. approval 2014).

As used herein, a "pembrolizumab variant" means a monoclonal antibody that comprises heavy chain and light chain sequences that are substantially identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions or the constant region, and optionally has a deletion of the C-terminal lysine residue of the heavy chain. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

Anti-PD-1 Antibodies and Antigen-Binding Fragments Thereof

In some embodiments, an anti-human PD-1 antibody or antigen binding fragment thereof for use in the compositions of the invention comprises a light chain variable region comprising three light chain CDRs of CDRL1, CDRL2 and CDRL3 and a heavy chain variable region comprising three heavy chain CDRs of CDRH1, CDRH2 and CDRH3.

In one embodiment of the invention, CDRL1 is SEQ ID NO:1, CDRL2 is SEQ ID NO:2, and CDRL3 is SEQ ID NO:3. In one embodiment, CDRH1 is SEQ ID NO:6, CDRH2 is SEQ ID NO: 7, and CDRH3 is SEQ ID NO:8. In one embodiment, the three light chain CDRs are SEQ ID NO:1, SEQ ID NO:2, and SEQ ID NO:3 and the three heavy chain CDRs are SEQ ID NO:6, SEQ ID NO:7 and SEQ ID NO:8.

Anti-PD-1 binding fragments of the compositions of the invention comprise a light chain variable region and a heavy chain variable region. In one embodiment of the compositions of the invention, the antibody or antigen binding fragment comprises a light chain variable region comprising or consisting of SEQ ID NO:4 and a heavy chain variable region comprising or consisting of SEQ ID NO:9.

In another embodiment, the compositions of the invention comprise an antibody or antigen binding fragment that has a $V_L$ domain and/or a $V_H$ domain with at least 95%, 90%, 85%, 80%, 75% sequence homology to one of the $V_L$ domains or $V_H$ domains described above, and exhibits specific binding to PD-1. In another embodiment, the antibody or antigen binding fragment of the compositions of the invention comprises $V_L$ and $V_H$ domains having up to 1, 2, 3, 4, or 5 or more amino acid substitutions, and exhibits specific binding to PD-1.

In any of the embodiments above, the anti-PD-1 antibody may be a full-length anti-PD-1 antibody that specifically binds human PD-1. In certain embodiments, the full-length anti-PD-1 antibody is selected from any class of immunoglobulins, including IgM, IgG, IgD, IgA, and IgE. Preferably, the antibody is an IgG antibody. Any isotype of IgG can be used, including $IgG_1$, IgG2, IgG3, and IgG4. Different constant domains may be appended to the $V_L$ and VH regions provided herein. For example, if a particular intended use of an antibody (or fragment) of the invention were to call for altered effector functions, a heavy chain constant domain other than IgG1 may be used. Although IgG1 antibodies provide for long half-life and effector functions, such as complement activation and antibody-dependent cellular cytotoxicity, such activities may not be desirable for all uses of the antibody. In such instances an IgG4 constant domain, for example, may be used.

In embodiments of the invention, the anti-PD-1 antibody comprises a light chain comprising or consisting of a sequence of amino acid residues as set forth in SEQ ID NO:5 and a heavy chain comprising or consisting of a sequence of amino acid residues as set forth in SEQ ID NO:10. In some compositions of the invention, the anti-PD-1 antibody is pembrolizumab, or pembrolizumab variant.

Ordinarily, amino acid sequence variants of the anti-PD-1 antibodies and antigen binding fragments of the invention will have an amino acid sequence having at least 75% amino acid sequence identity with the amino acid sequence of a reference antibody or antigen binding fragment (e.g. heavy chain, light chain, $V_H$, $V_L$, or humanized sequence), more preferably at least 80%, more preferably at least 85%, more preferably at least 90%, and most preferably at least 95, 98, or 99%. Identity or homology with respect to a sequence is defined herein as the percentage of amino acid residues in the candidate sequence that are identical with the anti-PD-1 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, DC; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, DC; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

Likewise, either class of light chain can be used in the compositions and methods herein. Specifically, kappa, lambda, or variants thereof are useful in the present compositions and methods.

TABLE 2

Exemplary PD-1 Antibody Sequences

| Antibody Feature | Amino Acid Sequence | SEQ ID NO. |
|---|---|---|
| Pembrolizumab Light Chain | | |
| CDR1 | RASKGVSTSGYSYLH | 1 |
| CDR2 | LASYLES | 2 |
| CDR3 | QHSRDLPLT | 3 |
| Variable Region | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIK | 4 |
| Light Chain | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 5 |
| Pembrolizumab Heavy Chain | | |
| CDR1 | NYYMY | 6 |
| CDR2 | GINPSNGGTNFNEKFKN | 7 |
| CDR3 | RDYRFDMGFDY | 8 |
| Variable Region | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSS | 9 |
| Heavy Chain | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | 10 |
| Heavy Chain | XVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG<br>X is pyroglutamate | 11 |
| Heavy Chain | XVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFDMGFDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK<br>X is pyroglutamate | 12 |

TABLE 2-continued

Exemplary PD-1 Antibody Sequences

| Antibody Feature | Amino Acid Sequence | SEQ ID NO. |
|---|---|---|
| Heavy Chain | QVQLVQSGVEVKKPGASVKVSCKASGYTFTNYYMYWV<br>RQAPGQGLEWMGGINPSNGGTNFNEKFKNRVTLTTDSST<br>TTAYMELKSLQFDDTAVYYCARRDYRFDMGFDYWGQG<br>TTVTVSSASTKGPSVFPLAPCSRSTSESTAALGCLVKDYF<br>PEPVTVSWNSGALTSGVHTFPAVLQSSGLYSLSSVVTVPS<br>SSLGTKTYTCNVDHKPSNTKVDKRVESKYGPPCPPCPAP<br>EFLGGPSVFLFPPKPKDTLMISRTPEVTCVVVDVSQEDPE<br>VQFNWYVDGVEVHNAKTKPREEQFNSTYRVVSVLTVLH<br>QDWLNGKEYKCKVSNKGLPSSIEKTISKAKGQPREPQVY<br>TLPPSQEEMTKNQVSLTCLVKGFYPSDIAVEWESNGQPE<br>NNYKTTPPVLDSDGSFFLYSRLTVDKSRWQEGNVFSCSV<br>MHEALHNHYTQKSLSLSLG | 13 |
| Heavy Chain | XVQLVQSGVEVKKPGASVKVSCKASGYTFTNYYMYWV<br>RQAPGQGLEWMGGINPSNGGTNFNEKFKNRVTLTTDSST<br>TTAYMELKSLQFDDTAVYYCARRDYRFDMGFDYWGQG<br>TTVTVSSASTKGPSVFPLAPCSRSTSESTAALGCLVKDYF<br>PEPVTVSWNSGALTSGVHTFPAVLQSSGLYSLSSVVTVPS<br>SSLGTKTYTCNVDHKPSNTKVDKRVESKYGPPCPPCPAP<br>EFLGGPSVFLFPPKPKDTLMISRTPEVTCVVVDVSQEDPE<br>VQFNWYVDGVEVHNAKTKPREEQFNSTYRVVSVLTVLH<br>QDWLNGKEYKCKVSNKGLPSSIEKTISKAKGQPREPQVY<br>TLPPSQEEMTKNQVSLTCLVKGFYPSDIAVEWESNGQPE<br>NNYKTTPPVLDSDGSFFLYSRLTVDKSRWQEGNVFSCSV<br>MHEALHNHYTQKSLSLSL<br>X is pyroglutamate | 14 |
| Heavy Chain | QVQLVQSGVEVKKPGASVKVSCKASGYTFTNYYMYWV<br>RQAPGQGLEWMGGINPSNGGTNFNEKFKNRVTLTTDSST<br>TTAYMELKSLQFDDTAVYYCARRDYRFDMGFDYWGQG<br>TTVTVSSASTKGPSVFPLAPCSRSTSESTAALGCLVKDYF<br>PEPVTVSWNSGALTSGVHTFPAVLQSSGLYSLSSVVTVPS<br>SSLGTKTYTCNVDHKPSNTKVDKRVESKYGPPCPPCPAP<br>EFLGGPSVFLFPPKPKDTLMISRTPEVTCVVVDVSQEDPE<br>VQFNWYVDGVEVHNAKTKPREEQFNSTYRVVSVLTVLH<br>QDWLNGKEYKCKVSNKGLPSSIEKTISKAKGQPREPQVY<br>TLPPSQEEMTKNQVSLTCLVKGFYPSDIAVEWESNGQPE<br>NNYKTTPPVLDSDGSFFLYSRLTVDKSRWQEGNVFSCSV<br>MHEALHNHYTQKSLSLSL | 15 |

Protein Expression

The methods of the invention for manufacturing the antibody involves culturing antibody-secreting mammalian cells. Such cultured mammalian cells are typically made by recombinant DNA technology involving transient or stable transfection, e.g., the pooled plasmid constructs (expression vectors) from the cloning step can be transfected into a plurality of host cells (e.g., mammalian, HEK 293 or CHO, bacterial, insect, yeast cells) for expression using a cationic lipid, polyethylenimine, Lipofectamine™, or Expi-Fectamine™, or electroporation. The skilled practitioner is aware of numerous suitable means for transfecting to achieve expression of recombinant antibodies. Alternatively, methods for stable genomic integration of expressions cassettes encoding the protein of interest can be employed to make a production cell line of protein-secreting mammalian cells. (See, e.g., Zhang, Crispr-Cas Systems and Methods for Altering Expression Of Gene Products, WO2014093661 A2; Frendewey et al., Methods and Compositions for the Targeted Modification of a Genome, U.S. Pat. No. 9,228,208 B2; Church et al., Multiplex Automated Genome Engineering, WO2008052101A2, U.S. Pat. No. 8,153,432 B2; Bradley et al., Methods Cells and Organisms, US2015/0079680 A1; Begemann et al., Compositions and Methods for Modifying Genomes, WO2017141173A2; Gill et al., Nucleic acid-guided nucleases, U.S. Pat. No. 9,982,279 B1; Minshull et al., Enhanced nucleic acid constructs for eukaryotic gene expression, U.S. Pat. No. 9,428,767B2, 9,580,697B2, 9,574,209B2; Minshull et al., DNA Vectors, Transposons And Transposases For Eukaryotic Genome Modification, U.S. Pat. No. 10,041,077B2).

In other embodiments, expression cassettes that efficiently integrate into eukaryotic transcriptionally active hot spots and ensure long term stable and consistent expression of the gene of interest (GOI) is described in WO2020068631. These expression cassettes can be transfected into various host CHO cell lines, including CHOK1SVTM (Lonza; Slough, U.K.), HD-BIOP1 (Horizon Discovery, U.K.), CHOZN® (Sigma-Aldrich, St. Louis, MO) and GS knock-out CHO host cell lines. In one embodiment, the expression vector comprises:

(a) a first expression cassette comprising the following elements in the order of upstream to downstream: a first insulator, an EASE, a promoter, a TPL, an insertion site for a Gene of Interest (GOI), an IRES, a polynucleotide encoding a eukaryotic selectable marker, a polyA signal, and a second insulator;

(b) two ITR sequences flanking the first expression cassette;

(c) a second expression cassette comprising a polynucleotide encoding a bacterial selectable marker; and (d) a bacterial plasmid origin of replication.

In one embodiment, the promotor is a SV40 promoter (Nature 273(5658):113-20 (1978), Proc. Natl. Acad. Sci. USA 81 (1):23-27 (1984), GenBank: J02400.1. In another embodiment, the promotor is hCMV immediate-early enhancer/promoter (GenBank X17403.1). In another embodiment, the ITR is piggyBac ITR. In one embodiment, the insulator is a Chicken β-globin HS4 insulator.

In one embodiment, the eukaryotic selectable marker is a neomycin phosphotransferase, a histidinol dehydrogenase, a hygromycin B phosphotransferase, a xanthine-guanine phosphoribosyltransferase, a dihydrofolate reductase, a tryptophan synthetase, a puromycin N-acetyl-transferase, a thymidine kinase, an adenine phosphoribosyl transferase, a glutamine synthetase, an adenosine deaminase, or metallothionein-1. In one embodiment, the eukaryotic selectable marker is a neomycin phosphotransferase. In another embodiment, the eukaryotic selectable marker is a glutamine synthetase. In certain embodiments of the various expression vectors provided herein, the bacterial selectable marker is an ampicillin resistance gene, a tetracycline resistance gene, a hygromycin resistance gene, a kanamycin resistance gene, a blasticidin resistance gene, or the like. In one embodiment, the bacterial selectable marker is an ampicillin resistance gene.

Upstream Cell Culture Process

The host cells used to produce the antibody in the invention can be cultured in a variety of cell culture media. Commercially available media such as CD-CHO liquid or CD-CHO AGT™ Powder (Life Technologies), Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; Wo90103430; WO 87/00195; or U.S. Patent Re. No. 30,985 may be used as culture media for the host cells. Any of these media may be supplemented with other ingredients as necessary at appropriate concentrations that would be known to those skilled in the art. For example, hormones and/or other growth factors (such as insulin, transferrin, or epidermal growth factor), salts (such as sodium chloride, sodium bicarbonate, calcium, iron, potassium, zinc, copper sulfate, manganese, magnesium, and phosphate), nucleotides (such as adenosine, adenine, thymidine, cytidine, guanosine, uridine, purine), any of the 20 amino acids (tyrosine, cysteine, cystine, glutamic acid), vitamin or supplements (choline, inositol, thiamine, folic acid, biotin, calcium, niacinamide, p-aminobenzoic acid, pyridoxine, riboflavin, thymidine, cyanocobalamin, pyruvate, lipoic acid, linoleic acid, selenite, glycine, putrescine, ethanolamine), selection agents that confer resistance or survival to selectable markers such as antibiotics (such as geneticin, neomycin, hygromycin B, puromycin, zeocin, Gentamycin™), trace elements (defined as inorganic compounds usually present at final concentrations in the micromolar range), and glucose, galactose or an equivalent energy source, such that the physiological conditions of the cell in, or on, the medium promote expression of the protein of interest by the host cell. Typically, cell culture medium for perfusion is more concentrated to allow for sustained growth of cells at higher density. In one embodiment, non-ionic surfactants such as Kolliphor® P188 at 2-10 g/L can be added to prevent cell death during the perfusion process and maintain high cell density and viability. See Xu et al., Bioprocess Biosyst Eng (2017) 40:1317-1326. In another embodiment, the copper concentration in the perfusion cell culture medium is 10-35 ppb. Depending on the cell density and cell uptake of copper, the copper concentration in the perfusion bioreactor can range from 1 to 35 ppb. The culture medium is preferably serum-free. In some embodiments, the aqueous medium is liquid, such that the host cells are cultured in a cell suspension within the liquid medium.

The culture conditions, such as temperature (for mammalian cells, typically, about 37°±1° C.), pH (typically, but not necessarily, the cell culture medium is maintained within the range of about pH 6.5-7.5), oxygenation, and the like, will be apparent to the ordinarily skilled artisan. In one embodiment, the dissolved oxygen level is about 15-100%, and the pH is about 6.7-7.3. Clearly, there will be small variations of the temperature, pH, or other culture condition over time, and from location to location through the culture vessel (i.e., the bioreactor) such that there is an operating range for these parameters. (See, also, e.g., Oguchi et al., pH Condition in temperature shift cultivation enhances cell longevity and specific hMab productivity in CHO culture, Cytotechnology. 52(3):199-207 (2006); Al-Fageeh et al., The cold-shock response in cultured mammalian cells: Harnessing the response for the improvement of recombinant protein production, Biotechnol. Bioeng. 93:829-835 (2006); Marchant, R. J. et al., Metabolic rates, growth phase, and mRNA levels influence cell-specific antibody production levels from in vitro cultured mammalian cells at sub-physiological temperatures, Mol. Biotechnol. 39:69-77 (2008)). Upon culturing the transfected or transformed host cells, the antibody is directly secreted into the cell culture medium (by employing appropriate secretory-directing signal peptides) and are harvested therefrom.

The perfusion bioreactor can be fluidly connected to an affinity chromatography step in an uninterrupted flow coming from the bioreactor (directly or indirectly via intervening unit operations, for example a surge vessel) to the affinity chromatography system. Some embodiments of the invention include a first single-use surge vessel (SUSV1) adapted to receive volumes of cell-free permeate removed from the perfusion bioreactor(s). These permeate volumes can be automatically and fluidly fed from the one or more perfusion bioreactor(s) into the SUSV1.

The invention provides a method of obtaining the purified compositions of the invention comprising the steps of:
a) perfusing mammalian host cells in cell culture medium in a perfusion bioreactor by applying a perfusion rate of at least about 0.25-6.0 vessel volume per day (vvd), wherein the host cell comprises a polynucleotide encoding the light chain variable domain and a polynucleotide encoding the heavy chain variable domain, or a polynucleotide encoding the light chain variable domain and the heavy chain variable domain of the antibody or antigen binding fragment of the anti-human PD-1 antibody;
b) continuously harvesting the antibody from the cell culture broth to obtain a harvest cell culture fluid;
c) optionally, transferring the harvest cell culture fluid (HCCF) to a surge vessel for a residence time of about 0.5 to 8 hours;
d) continuously purifying the harvest cell culture fluid with an affinity chromatography step to obtain the purified composition.

In one embodiment, the above method comprises the following steps before step a):
(i) inoculating a perfusion bioreactor with mammalian host cells in a cell culture medium at a cell density of about $0.2\text{-}0.6 \times 10^6$ cells/ml, ii) growing the mammalian cells in a cell culture medium to a cell density of about 1.0 to 6.0×10$^6$ cells/ml in a perfusion bioreactor.

In one embodiment, in step i) the cell density is about 0.20 to 0.6×10$^6$ cells/ml on Day 1. In one embodiment, in step i) the cell density is about 0.25 to 0.5×10$^6$ cells/ml on Day 1. In another embodiment, in step i) the cell density is about 0.4 to 0.5×10$^6$ cells/ml on Day 1. In another embodiment, in step a) the perfusion is initiated on Day 3. In another embodiment, in step a) the perfusion is initiated at a cell density of about 2 to 10×10$^6$ cells/ml. In another embodiment, in step a) the perfusion is initiated at a cell density of about 4 to 8×10$^6$ cells/ml. In another embodiment, step (ii) is growing the mammalian host cells in a cell culture medium to a cell density of about 2.0 to 6.0×10$^6$ cells/ml in a perfusion bioreactor.

The perfusion rate may initiate at about 0.5 vvd, and can be continuously, gradually or incrementally increased from about 0.5 vvd to 6 vvd. In one embodiment, in step a) the perfusion rate is at about 0.5 vvd to 4 vvd. In one embodiment, in step a) the perfusion rate is at about 0.5 vvd to 2 vvd. Preferably, the perfusion rate is kept constant after reaching the target. Alternatively, the perfusion rate can be adjusted throughout the continuous manufacturing process depending on the continuously measured viable cell density. In one embodiment, the perfusion rate is about 0.5 vvd on Day 3, about 1 vvd on Day 4 and about 2 vvd on Day 5. In a further embodiment, step d) is performed on or after Day 5. In a further embodiment, cell bleeding is performed to maintain a specific cell density, for example about 80 to 100×10$^6$ cells/ml, or capacitance value (about 70-90 or 80 pF/cm). In one embodiment, the maximum cell density is at about 80-100×10$^6$ cells/ml during perfusion. In one embodiment, the maximum cell density is at about 100×10$^6$ cells/ml during perfusion. In one embodiment, the mammalian host cell is CHO cell. In another embodiment, the perfusion cell culture medium has a copper concentration of 10-35 ppb. In a further embodiment, the copper concentration in the perfusion bioreactor ranges from 1 to 35 ppb.

In another aspect, continuous harvesting is performed by setting a constant permeate rate to obtain a cell-free permeate through a hollow fiber membrane connected to the perfusion bioreactor. In one embodiment, the perfusion rate is equal to the sum of the permeate rate and cell bleed rate. A typical perfusion system with feed stream, perfusion stream and cell bleeding stream is described in Goudar, C. T. & Chen, C. & Le, H. (2015). SBE special section: Biopharmaceuticals—Continuous processing in upstream operations. p111.

Downstream Process

The compositions of the invention from the upstream process may further undergo continuous or semi-continuous downstream purification, or a downstream batch purification process, to further purify the antibody or antigen-binding fragment composition.

Affinity chromatography separates molecules based on a highly specific interaction between the molecule of interest and the functional group of the resin, such as interaction between antigen and antibody, enzyme and substrate, receptor and ligand, or protein and nucleic acid, etc. Some commonly used affinity chromatographic resins include protein A or protein G resin to purify antibodies, avidin biotin resin to purify biotin/avidin and their derivatives, glutathione resin to purify GST-tagged recombinant proteins, heparin resin to separate plasma coagulation proteins, IMAC resin to purify proteins that specifically interact with the metal ions, etc. Operating conditions of each affinity chromatography depend on the mechanism of the interaction and factors that affect the interaction. Commercial affinity chromatographic resins include but are not limited to MabSelect Sure, UNOsphere SUPrATM, Affi-Gel®, and Affi-Prep®. In one embodiment, the affinity chromatography step is protein A chromatography performed in bind and elute mode.

In one embodiment, the harvest cell culture fluid is purified with a Protein A affinity chromatography comprising the steps of:
  a) binding the HCCF to a stationary phase;
  b) eluting the antibody or antigen binding fragment from the Protein A stationary phase with an elution solution;
  c) optionally, cleaning and sanitizing the stationary phase for repeated cycling.

In one embodiment, prior to step (a), equilibrating the stationary phase with an equilibration solution is performed. In one embodiment, one or more impurities are in the flow-through of step a).

In another aspect of the method, after step a) but prior to step b), the method further comprises the step of washing the stationary phase with one or more wash solutions. In one embodiment, one or more impurities are removed from the wash step. In one embodiment, the wash solution or elution solution comprises a salt, preferably a monovalent metal ion salt, such as NaCl or KCl. In one embodiment, the wash solution comprises about 400-600 mM NaCl or KCl. In another embodiment, the wash solution comprises about 500 mM NaCl or KCl. In another embodiment, the wash solution comprises about 400-500 mM NaCl or KCl. In a further embodiment, a first, second and third wash solution comprises about 5-20 mM Sodium Phosphate and the second wash solution further comprises about 400-600 mM NaCl or KCl. In a further embodiment, a first, second and third wash solution comprises about 10 mM Sodium Phosphate and the second wash solution further comprises about 500 mM NaCl or KCl.

In one embodiment, the pH of the wash or elution solution is about 6-7. In one embodiment, the pH of the wash or elution solution is about 6.5. In another embodiment, the elution solution comprises about 5-50 mM Sodium Acetate. In another embodiment, the elution solution comprises about 5-30 mM Sodium Acetate. In another embodiment, the elution solution comprises about 20 mM Sodium Acetate.

In another aspect, the elution solution comprises about 5-50 mM Sodium Acetate. In another embodiment, the elution solution comprises about 5-30 mM Sodium Acetate. In another embodiment, the elution solution comprises about 20 mM Sodium Acetate. In one embodiment, the elution solution has a pH of about 3.5-3.6. In another embodiment, the elution solution has a pH of about 3-4.

In one embodiment, the affinity chromatography is operated in a continuous multi-column chromatography (at least two, three or four columns) system allowing for uninterrupted flow of the HCCF to the chromatography skid.

In one embodiment, the perfusion bioreactor or perfusion system comprising the HCCF is fluidly connected indirectly or directly to the affinity chromatography. In one embodiment, the affinity chromatography is fluidly connected to the perfusion bioreactor.

In another embodiment, the perfusion bioreactor or system comprising the HCCF is fluidly connected through a surge vessel to the affinity chromatography. The surge vessel is sized in such a manner to control the residence time a fluid control volume spends in the surge vessel. In some embodiments of the invention, the mean residence time is 0.5-30 hours. In some embodiments of the invention, the mean residence time is 0.5-20 hours. In some embodiments of the invention, the mean residence time is 0.5-8 hours. In some embodiments, the mean residence time is 2 hrs. In some embodiments, the mean residence time is 1 hr. In some embodiments, the mean residence time is 0.5 hr. The HCCF can be stored at 4-25° C. in the surge vessel. In one embodiment, the HCCF flow rate to the surge vessel equals the feed rate from the surge vessel to the continuous multi-column chromatography system. Alternatively, the HCCF can be stored in a container at −40 to −80° C. before being fed to the affinity chromatography. In one embodiment, the antibody is protected from light during storage in the surge vessel or container.

In a further embodiment, the affinity chromatography is followed by one or more steps of a viral inactivation, depth filtration, a second chromatography, a third polishing chromatography, viral filtration, ultrafiltration, diafiltration, single pass-tangential flow filtration and an in-line diafiltration, optionally fluidly connected, or fluidly connected through a surge vessel or connected through a holding vessel.

In one aspect, the affinity chromatography is fluidly connected in an uninterrupted flow to, a viral inactivation system, and optionally, in an uninterrupted flow to depth filtration, fluidly connected to a second chromatography system, an optional third polishing chromatography system, viral filtration system, and ultrafiltration/diafiltration system, all in an uninterrupted flow to the afore-mentioned upstream processing steps and successively to each other, with optional intervening surge vessels. See FIG. 1C of WO2020168315. The final ultrafiltration step may be comprised of a single pass-tangential flow filtration step and an in-line diafiltration step operated either fluidly connected or through an optional surge vessel to maintain continuity from the affinity chromatography step through the in-line diafiltration product.

In another aspect, the affinity chromatography is fluidly connected in an uninterrupted flow to, a viral inactivation system, and optionally in an uninterrupted flow to depth filtration system, a holding vessel (HV1) for temporary storage of virally inactivated product pool; a second chromatography system, an optional third polishing chromatography system, and ultrafiltration/diafiltration system, successively fluidly connected to each other in an uninterrupted flow or in batch mode, with optional intervening surge vessels or holding vessels (i.e., holding vessels if there are two or more batch steps or operations), as the case may be. See for example FIG. 1D of WO2020168315. The final ultrafiltration step may be comprised of a single pass-tangential flow filtration step and an in-line diafiltration step operated either directly connected or through an optional surge vessel to maintain continuity from the affinity chromatography step through the in-line diafiltration product.

In some embodiments of the invention, the affinity chromatography step is followed by a viral inactivation step. For viral inactivation, a collection of affinity chromatography elutions are pooled into one of two viral inactivation pooling vessels. After a discrete number of elutions have been collected in the pooling vessel, the pool volume undergoes an automated pH adjustment from elution pH, to the viral inactivation pH (pH=3.4-3.7) by adding an acid solution, followed by an adjustment to a neutral pH through the addition of a base. In some embodiments, the neutralization pH is 4.0-7.5. In some embodiments, the neutralization pH is 4-6. In some embodiments, the neutralization pH is 7.2. During this automated adjustment cycle, new affinity chromatography elutions are collected in the second viral inactivation pooling vessel. Switching between the two viral inactivation pooling vessel allows for the unit operation to operate continuously. In some embodiments of the invention the viral inactivated product (VIP) is transferred into a surge vessel feeding other downstream unit operations continuously.

In some embodiments of the invention, operations downstream of the viral inactivation system/neutralization system involve continuous processing by transferring the VIP into a surge vessel which can feed a second chromatography step or optionally be filtered by depth filtration to yield a filtered virally inactivated product pool (FVIP). Semi-continuous flow in these unit operations is maintained by cycling either depth filtration consumables or the second chromatography column at regular intervals. In these instances, flow is paused during flushing and regeneration of the phases between consumable switch outs and during non-load steps of the chromatography phase.

In some embodiments of the invention, operations downstream of the viral inactivation system/neutralization system involve continuous processing of the virally inactivated product pool (which can optionally also be filtered by depth filtration to yield a filtered virally inactivated product pool (FVIP)); in such embodiments, the virally inactivated product pool is collected in a collection vessel, and in subsequent batch-wise steps or operations, the purified product pool or virus-free filtrate can optionally be collected in other collection vessels between steps. In such discrete operation, batch-wise, or batch mode, processing, the collection vessel(s) or interchangeably "collection tank(s)," from one step (which in certain embodiments may also be deemed a "feed tank(s)" for the subsequent step) lack the automated controls of a surge vessel, and although the collection vessel (or feed tank) may physically resemble a surge vessel, such a collection vessel (or interchangeably, "collection tank") or feed tank, is called a "holding vessel" or, interchangeably an "HV" (e.g., HV1, HV2, HV3, HV4, or HV5). A "holding vessel" can be a single-use holding vessel (SUHV), distinct from a single-use collection vessel (SUCV, e.g., SUCV1 or SUCV2) in a continuous or semi-continuous format set of manufacturing process steps or operations. See FIG. 1D of WO2020168315.

The affinity chromatography step can be followed by a second and/or third chromatography steps to remove for example, protein aggregates, host cell protein or DNA. IEX chromatography separates molecules based on net charge of the molecules. Separation occurs as a result of competition between the charged molecule of interest and counter ions for oppositely charged ligand groups on the IEX chromatographic resin. Strength of the binding of the molecule to the IEX resin depends on the net charge of the molecules, which is affected by operating conditions, such as pH and ionic strength. IEX resins include AEX resins and CEX resins. AEX resins may contain substituents such as diethylaminoethyl (DEAE), trimethylaminoethyl (TMAE), quaternary aminoethyl (QAE) and quaternary amine (O) groups. CEX resins may contain substituents such as carboxymethyl (CM), sulfoethyl (SE), sulfopropyl (SP), phosphate (P) and sulfonate (S). Cellulosic IEX resins such as DE23, DE32, DE52, CM-23, CM-32 and CM-52 are available from Whatman Ltd. Maidstone, Kent, U.K. Sephadex-based and cross-linked IEX resins are also known. For example, DEAE-, QAE-, CM-, and SP-Sephadex, and DEAE-, Q-, CM- and S-Sepharose, and Sepharose are all available from GE Healthcare, Piscataway, NJ Further, both DEAE and CM derived ethylene glycol-methacrylate copolymer such as TOYOPEARLTM DEAE-650Sor M and TOYOPEARLTM CM-650S or M are available from Toso Haas Co., Philadelphia, PA POROSTM HS, POROSTM HQ, POROSTM XS are available from Thermo Fisher Scientific, Waltham, MA. In one embodiment, the second chromatography step is AEX chromatography performed in flow-through mode at pH about 6.5-8.0. In one embodiment, the pH is about 6.5 to 7.5.

Following purification through the chromatography steps, the antibody or antigen-binding fragment may be processed through a series of filtration steps including nanofiltration for virus removal and ultrafiltration for concentration and buffer exchange. The nanofiltration may be operated batch-wise through the use of holding vessels or continuously by cycling nanofiltration membranes at an appropriate frequency. The ultralfiltration steps may be performed conventionally in batch mode by feeding the unit operation from a holding vessel containing virally filtered nano-filtration product. Alternatively, the ultrafiltration may be conducted continuously by using single pass ultrafiltration followed by in-line diafiltration either directly connected or through the use of an intermediate surge vessel.

Purified Compositions

The invention provides a composition comprising an anti-human PD-1 antibody or antigen-binding fragment thereof with less than about 3.0% oxidation of Methionine 105, wherein the anti-human PD-1 antibody or antigen binding fragment thereof comprises a light chain variable region comprising three light chain CDRs comprising CDRL1 of SEQ ID NO:1, CDRL2 of SEQ ID NO:2 and CDRL3 of SEQ ID NO:3 and a heavy chain variable region comprising three heavy chain CDRs of CDRH1 of SEQ ID NO:6, CDRH2 of SEQ ID NO:7 and CDRH3 SEQ ID NO:8. In one embodiment, the anti-human PD-1 antibody or antigen binding fragment thereof comprises a light chain variable region which comprises the amino acid sequence set forth in SEQ ID NO:4, and a heavy chain variable region comprising the amino acid sequence set forth in SEQ ID NO:9. In another embodiment, the anti-human PD-1 antibody comprises a light chain comprising the amino acid sequence set forth in SEQ ID NO:5 and a heavy chain comprising the amino acid sequence set forth in SEQ ID NO:10. In a further embodiment, the anti-human PD-1 antibody consists of two light chains and two heavy chains, wherein the two light chains consists of the amino acid sequence set forth in SEQ ID NO:5, wherein the two heavy chains consist of the amino acid sequence set forth in any one of SEQ ID NOs:10-15, or a combination thereof. In a further embodiment, the anti-human PD-1 antibody consists of two light chains and two heavy chains, wherein the two light chains consist of the amino acid sequence set forth in SEQ ID NO: 5, wherein the two heavy chains consist of the amino acid sequence set forth in SEQ ID NO: 11.

In one embodiment, the oxidation of Methionine 105 is about 0.2-3.0%. In one embodiment, the oxidation of Methionine 105 is 0.2-3.0%. In another embodiment, the oxidation of Methionine 105 is about 0.5-3.0%. In another embodiment, the oxidation of Methionine 105 is 0.5-3.0%. In another embodiment, the oxidation of Methionine 105 is about 0.5-2.5%. In another embodiment, the oxidation of Methionine 105 is 0.5-2.5%. In another embodiment, the oxidation of Methionine 105 is about 0.5-2.0%. In another embodiment, the oxidation of Methionine 105 is 0.5-2.0%. In another embodiment, the oxidation of Methionine 105 is about 0.5-1.5%. In another embodiment, the oxidation of Methionine 105 is 0.5-1.5%.

In one embodiment, the % Methionine oxidation is measured by reduced peptide mapping followed by liquid chromatography and mass spectroscopy. In another embodiment, the % Methionine oxidation is measured by hydrophobic interaction chromatography (HIC). In one embodiment, the HIC method is performed by an HPLC with a Tosoh Phenyl-5PW column, and a mobile phase containing a gradient of the following components (mobile phase A: 5 mM sodium phosphate in 2% acetonitrile, pH 7.0; mobile phase B: 400 mM ammonium sulfate, 5 mM sodium phosphate in 2% acetonitrile, pH 6.9). The % Met 105 oxidation is determined by the percentage of pre-main peaks (containing Met 105 oxidation) in relation to the total of pre-main, peaks and post peaks.

In a further aspect, the invention provides a composition comprising an anti-PD-1 antibody main species comprising an antibody consisting of two heavy chains and two light chains, each heavy chain consisting of the amino acid sequence of SEQ ID NO: 11, and each light chain consisting of the amino acid sequence of SEQ ID NO: 5, and acidic species of the anti-PD-1 antibody main species, wherein the amount of acidic species is about 1.0-12.0%. In another aspect, the invention provides a composition comprising an anti-PD-1 antibody main species comprising an antibody consisting of two heavy chains and two light chains, each heavy chain consisting of the amino acid sequence of SEQ ID NO: 11, and each light chain consisting of the amino acid sequence of SEQ ID NO: 5, and acidic and basic species of the anti-PD-1 antibody main species, wherein the amount of main species is about 65-85%. In a further aspect, the invention provides a composition comprising an anti-PD-1 antibody main species produced from a Chinese Ovary cell that comprises a polynucleotide encoding a light chain and a polynucleotide encoding a heavy chain, or a polynucleotide encoding a light chain and a heavy chain, wherein the heavy chain consists of the amino acid sequence of SEQ ID NO: 10, 13 or 15, and the light chain consists of the amino acid sequence of SEQ ID NO: 5, and acidic species of the anti-PD-1 antibody main species thereof, wherein the amount of acidic species is 1.0-12.0%. In one embodiment, the amount of main species is about 65-80%. In another embodiment, the amount of main species is at about 70-80%. In another embodiment, the amount of main species is at about 70-85%. In a further embodiment, the amount of main species is at about 70-75%. In a further embodiment, the amount of main species is at least about 65%.

In another aspect, the invention provides a composition comprising an anti-PD-1 antibody main species comprising an antibody consisting of two heavy chains and two light chains, each heavy chain consisting of the amino acid sequence of SEQ ID NO: 11, and each light chain consisting of the amino acid sequence of SEQ ID NO: 5, and acidic species of the anti-PD-1 antibody main species, wherein the amount of acidic species is 1.0-12.0%. In another aspect, the invention provides a composition comprising an anti-PD-1 antibody main species comprising an antibody consisting of two heavy chains and two light chains, each heavy chain consisting of the amino acid sequence of SEQ ID NO: 11, and each light chain consisting of the amino acid sequence of SEQ ID NO: 5, and acidic and basic species of the anti-PD-1 antibody main species, wherein the amount of main species is 65-85%. In a further aspect, the invention provides a composition comprising an anti-PD-1 antibody main species produced from a Chinese Ovary cell that comprises a polynucleotide encoding a light chain and a polynucleotide encoding a heavy chain, or a polynucleotide encoding a light chain and a heavy chain, wherein the heavy chain consists of the amino acid sequence of SEQ ID NO: 10, 13 or 15, and the light chain consists of the amino acid sequence of SEQ ID NO: 5, and acidic species of the anti-PD-1 antibody main species thereof, wherein the amount of acidic species is 1.0-12.0%. In one embodiment, the amount of main species is 65-80%. In one embodiment, the amount of main species is 65-80%. In another embodiment, the amount of main species is at 70-80%. In another embodiment, the amount of main species is at 70-85%. In a further embodiment, the amount of main species is at 70-75%. In a further embodiment, the amount of main species is at least 65%.

In one embodiment, the amount of acidic species is about 6-10%. In one embodiment, the amount of acidic species is about 7-9%. In another embodiment, the amount of acidic1 species is about 1-4%. In another embodiment, the amount of acidic1 species is about 2-4%. In another embodiment, the amount of acidic1 species is about 2-3%. In a further embodiment, the amount of acidic variants species is about 1-5%. In a further embodiment, the amount of acidic variants species is about 2-5%. In a further embodiment, the amount of acidic variants species is about 2-4%. In yet another embodiment, the composition further comprises basic species of about 12-27%. In yet another embodiment, the composition further comprises basic species of about 15-20%. In yet a further embodiment, the amount of basic 1 species is about 4-12%. In yet a further embodiment, the amount of basic 1 species is about 8-12%.

In one embodiment, the amount of acidic species is 6-10%. In one embodiment, the amount of acidic species is 7-9%. In another embodiment, the amount of acidic1 species is 1-4%. In another embodiment, the amount of acidic1 species is 2-4%. In another embodiment, the amount of acidic1 species is 2-3%. In a further embodiment, the amount of acidic variants species is 1-5%. In a further embodiment, the amount of acidic variants species is 2-5%. In a further embodiment, the amount of acidic variants species is 2-4%. In yet another embodiment, the composition further comprises basic species of 12-27%. In yet another embodiment, the composition further comprises basic species of 15-20%. In yet a further embodiment, the amount of basic 1 species is 4-12%. In yet a further embodiment, the amount of basic 1 species is 8-12%.

In one aspect of measuring the main species, acidic species or basic species, a cation exchange chromatography is used. In one embodiment, the cation exchange column is ProPac WCX-10, Sepax Proteomix WCX-NP1.7, Thermo MAbPac SCX-10G or Thermo MAbPac SCX50G. One skilled in the art would understand to use any industry equivalent to the foregoing columns. In another embodiment, a weak cation exchange column with a carboxylate functional group is used. In a further embodiment, the weak cation exchange column with a carboxylate functional group has a particle size 10 um, diameter 4 mm, length 250 mm. In one embodiment, the Thermo Scientific ProPac WCX-10 column is used for the cation ion exchange method. In another embodiment, a Thermo Scientific ProPac WCX-10 column is used at 35° C., with a Mobile Phase (A) 24 mM MES pH 6.1 with 4% acetonitrile, and mobile phase (B) 20 mM sodium phosphate, 95 mM NaCl pH 8.0 with 4% acetonitrile, and the chromatogram is generated using detection at 280 nm. In one embodiment, a non-linear gradient is used with: 22%-22% B for 0-0.6 min; 22%-29% B for 0.6-15.0 min; 29%-70% B for 15.0-30.0 min; 70%-100% B for 30.0-30.5 min; and 100%-100% B from 30.5-33.0 min. In a further embodiment, the cation ion exchange method is described in Example 5. In another aspect of measuring the main species, acidic species or basic species, an anion exchange chromatography is used.

In one embodiment, the composition is a cell culture fluid from a perfusion bioreactor. In another embodiment, the composition is a harvested cell culture fluid. In another embodiment, the composition is a cell-free permeate. In another embodiment, the composition is a harvested cell culture fluid that was purified by Protein A and/or Anion exchange chromatography. In another embodiment, the antibody was produced from mammalian cells. In another embodiment, the antibody was produced from CHO cells.

In another aspect of the above embodiments, the composition comprises about 5-200 mg/ml of the antibody. In one embodiment, the composition comprises about 25-165 mg/ml of the antibody. In one embodiment, the composition comprises about 25 mg/ml of the antibody. In one embodiment, the composition comprises about 120 mg/ml of the antibody. In one embodiment, the composition comprises about 130 mg/ml of the antibody. In one embodiment, the composition comprises about 165 mg/ml of the antibody. In one embodiment, a pharmaceutical composition comprises about 165 mg/mL of the anti-human PD-1 antibody, about 10 mM histidine buffer; about 10 mM L-methionine, or a pharmaceutically acceptable salt thereof, about 7% w/v sucrose, and about 0.02% w/v polysorbate 80. In one embodiment, a pharmaceutical composition comprises about 130 mg/mL of the anti-human PD-1 antibody, about 10 mM histidine buffer, about 10 mM L-methionine, or a pharmaceutically acceptable salt thereof, about 7% w/v sucrose, and about 0.02% w/v polysorbate 80. In another embodiment, a pharmaceutical composition comprises about 25 mg/mL of the anti-human PD-1 antibody, about 10 mM histidine buffer, about 7% w/v sucrose, and about 0.02% w/v polysorbate 80.

In another aspect of the above embodiments, the composition comprises about 200-800 mg of the antibody. In one embodiment, the composition comprises about 200 mg of the antibody. In one embodiment, the composition comprises about 400 mg of the antibody.

Methods of Use

The invention also relates to a method of treating cancer in a subject, the method comprising administering an effective amount of any of the compositions of the invention; i.e., any composition described herein, to the subject. In some embodiments of this method, the composition is administered to the subject by subcutaneous administration.

In any of the methods of the invention, the cancer can be selected from the group consisting of: melanoma, lung cancer, head and neck cancer, bladder cancer, breast cancer, gastrointestinal cancer, multiple myeloma, hepatocellular cancer, merkel cell carcinoma, cutaneous squamous cell carcinoma, lymphoma, renal cancer, mesothelioma, ovarian cancer, esophageal cancer, anal cancer, biliary tract cancer, colorectal cancer, endometrial cancer, cervical cancer, thyroid cancer, salivary cancer, prostate cancer (e.g. hormone refractory prostate adenocarcinoma), pancreatic cancer, colon cancer, liver cancer, thyroid cancer, glioblastoma, glioma, and other neoplastic malignancies.

In one embodiment, the cancer is melanoma, non-small cell lung cancer, head and neck cancer, urothelial cancer, breast cancer, gastric cancer, gastroesophageal junction adenocarcinoma, multiple myeloma, hepatocellular cancer, merkel cell carcinoma, renal cell carcinoma, endometrial carcinoma, cutaneous squamous cell carcinoma, non-Hodgkin lymphoma, Hodgkin lymphoma, mesothelioma, ovarian cancer, small cell lung cancer, esophageal cancer, anal cancer, biliary tract cancer, colorectal cancer, cervical cancer, thyroid cancer, salivary cancer, prostate cancer, glioblastoma, Tumor Mutational Burden-High or MSI-H cancer.

In some embodiments the lung cancer is non-small cell lung cancer (NSCLC). In some embodiments the lung cancer is squamous non-small cell lung cancer. In some embodiments the lung cancer is non-squamous non-small cell lung cancer. In one embodiment, the NSCLC is metastatic.

In alternate embodiments, the lung cancer is small-cell lung cancer (SCLC). In one embodiment, the SCLC is metastatic.

In some embodiments, the lymphoma is Hodgkin lymphoma.

In other embodiments, the lymphoma is non-Hodgkin lymphoma. In particular embodiments, the lymphoma is mediastinal large B-cell lymphoma. In some embodiments, the lymphoma is diffuse large B-cell lymphoma (DLBCL).

In some embodiments, the breast cancer is triple negative breast cancer.

In further embodiments, the breast cancer is ER+/HER2− breast cancer.

In some embodiments, the bladder cancer is urothelial cancer.

In some embodiments, the head and neck cancer is nasopharyngeal cancer. In some embodiments, the cancer is thyroid cancer. In other embodiments, the cancer is salivary cancer. In other embodiments, the cancer is squamous cell carcinoma of the head and neck.

In some embodiments, the cancer is metastatic colorectal cancer with high levels of microsatellite instability (MSI-H).

In some embodiments, the cancer is a solid tumor with a high level of microsatellite instability (MSI-H).

In some embodiments, the cancer is a solid tumor with a high mutational burden. In one embodiment, the Tumor Mutation Burden (TMB) is ≥10 mutations/megabase as determined by an FDA approved test. In one embodiment, the tumor is metastatic or unresectable.

In some embodiments, the cancer is selected from the group consisting of: melanoma, non-small cell lung cancer, relapsed or refractory classical Hodgkin lymphoma, head and neck squamous cell carcinoma, urothelial cancer, esophageal cancer, gastric cancer, DLBCL and hepatocellular cancer.

In other embodiments of the above treatment methods, the cancer is a Heme malignancy. In certain embodiments, the Heme malignancy is acute lymphoblastic leukemia (ALL), acute myeloid leukemia (AML), chronic lymphocytic leukemia (CLL), chronic myeloid leukemia (CML), DLBCL, EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin lymphoma (NHL), or small lymphocytic lymphoma (SLL).

Malignancies that demonstrate improved disease-free and overall survival in relation to the presence of tumor-infiltrating lymphocytes in biopsy or surgical material, e.g. melanoma, colorectal, liver, kidney, stomach/esophageal, breast, pancreas, and ovarian cancer are encompassed in the methods and treatments described herein. Such cancer subtypes are known to be susceptible to immune control by T lymphocytes. Additionally, included are refractory or recurrent malignancies whose growth may be inhibited using the antibodies described herein.

In some embodiments, the compositions of the invention are administered to a subject having a cancer characterized by elevated expression of PD-L1 and/or PD-L2 in tested tissue samples, including: ovarian, renal, colorectal, pancreatic, breast, liver, gastric, esophageal cancers and melanoma. Additional cancers that can benefit from treatment with anti-PD-1 antibodies such as humanized anti-PD-1 antibody pembrolizumab include those associated with persistent infection with viruses such as human immunodeficiency viruses, hepatitis viruses class A, B and C, Epstein Barr virus, human papilloma viruses that are known to be causally related to for instance Kaposi's sarcoma, liver cancer, nasopharyngeal cancer, lymphoma, cervical, vulval, anal, penile and oral cancers.

In one embodiment, the invention comprises a method of treating cancer in a human patient comprising administering any composition of the invention to the patient.

In one embodiment, the invention comprises a method of treating unresectable or metastatic melanoma in a human patient comprising administering any composition of the invention to the patient.

In one embodiment, the invention comprises a method of treating metastatic non-small cell lung cancer (NSCLC) in a human patient comprising administering a composition of the invention to the patient. In specific embodiments, the patient has a tumor with high PD-L1 expression [(Tumor Proportion Score (TPS)≥50%)]. In other embodiments, the patient has a tumor with PD-L1 expression (TPS≥1%). In still other embodiments, the patient was or was not previously treated with platinum-containing chemotherapy. In specific embodiments, the patient had disease progression on or after receiving platinum-containing chemotherapy. In one embodiment, the NSCLC is metastatic or Stage III.

In certain embodiments, the PD-L1 TPS is determined by an FDA-approved test.

In certain embodiments, the patient's tumor has no EGFR or ALK genomic aberrations.

In certain embodiments, the patient's tumor has an EGFR or ALK genomic aberration and had disease progression on or after receiving treatment for the EGFR or ALK aberration(s) prior to receiving the compositions of the invention.

In certain embodiments, the patient has a tumor with PD-L1 expression CPS≥1%.

In one embodiment, the invention comprises a method of treating nonsquamous non-small cell lung cancer (NSCLC), wherein the method comprises administering a composition of the invention, pemetrexed and platinum chemotherapy to the patient. In one embodiment, the invention comprises a method of treating nonsquamous non-small cell lung cancer (NSCLC) in a human patient comprising: (1) administering a composition of the invention to the patient, and (2) administering pemetrexed and carboplatin to the patient. In specific embodiments, the patient was not previously treated with an anti-cancer therapeutic prior to starting the combination treatment regimen with the composition of the invention, pemetrexed and carboplatin. In a certain embodiments, the patient has metastatic nonsquamous non-small cell lung cancer.

In certain embodiments, pemetrexed is administered to the patient in an amount of 500 mg/m². In sub-embodiments, pemetrexed is administered to the patient via intravenous infusion every 21 days. In specific embodiments, the infusion time is about 10 minutes.

In embodiments of the invention where the patient is treated with a composition of the invention in combination with pemetrexed, the invention further comprises administering about 400 μg to about 1000 μg of folic acid to the patient once per day, beginning about 7 days prior to administering pemetrexed to the patient and continuing until about 21 days after the patient is administered the last dose of pemetrexed. In certain embodiments the folic acid is administered orally. In some embodiments, the invention further comprises administering about 1 mg of vitamin $B_{12}$ to the patient about 1 week prior to the first administration of pemetrexed and about every three cycles of pemetrexed administration (i.e., approximately every 9 weeks). In certain embodiments the vitamin $B_{12}$ is administered intramuscularly. In certain embodiments, the invention further comprises administering about 4 mg of dexamethasone to the patient twice a day on the day before, the day of, and the day after pemetrexed administration. In certain embodiments the dexamethasone is administered orally.

In one embodiment, the invention comprises a method of treating squamous non-small cell lung cancer (NSCLC) in a human patient comprising: (1) administering a composition of the invention to the patient, and (2) administering paclitaxel or protein-bound paclitaxel and carboplatin to the patient. In specific embodiments, the patient was not previously treated with an anti-cancer therapeutic prior to starting the combination treatment regimen. In certain embodiments, the patient has metastatic squamous non-small cell lung cancer.

In one embodiment, the invention comprises a method of treating recurrent or metastatic head and neck squamous cell cancer (HNSCC) in a human patient comprising administering any composition of the invention to the patient. In certain embodiments, the patient was previously treated with platinum-containing chemotherapy. In certain embodiments, the patient had disease progression on or after platinum-containing chemotherapy. In specific embodiments, the patient's tumor expresses PD-L1 [Combined Positive Score (CPS)≥1]. In one embodiment, the treatment is in combination with platinum and FU.

In one embodiment, the invention comprises a method of treating refractory classical Hodgkin lymphoma (cHL) in a human patient comprising administering a composition of the invention to the patient. In certain embodiments, the patient has relapsed after 2 or more lines of therapy for cHL. In specific embodiments, the patient is an adult patient. In alternative embodiments, the patient is a pediatric patient.

In one embodiment, the invention comprises a method of treating locally advanced or metastatic urothelial carcinoma in a human patient comprising administering a composition of the invention to the patient. In certain embodiments, the patient is not eligible for cisplatin-containing chemotherapy. In certain embodiments, the patient has disease progression during or following platinum-containing chemotherapy or within 12 months of neoadjuvant or adjuvant treatment with platinum-containing chemotherapy. In specific embodiments, the patient's tumor expresses PD-L1 [Combined Positive Score (CPS)≥1]. In one embodiment, the patients have Bacillus Calmette-Guerin (BCG)-unresponsive, high risk, non-muscle invasive bladder cancer.

In one embodiment, the invention comprises a method of treating unresectable or metastatic, microsatellite instability-high (MSI-H) or mismatch repair deficient solid tumors in a human patient comprising administering a composition of the invention to the patient. In specific embodiments, the patient had disease progression following prior anti-cancer treatment.

In one embodiment, the invention comprises a method of treating unresectable or metastatic, microsatellite instability-high (MSI-H) or mismatch repair deficient solid tumors or colorectal cancer in a human patient comprising administering a composition of the invention. In specific embodiments, the patient had disease progression following prior treatment with a fluoropyrimidine, oxaliplatin, and irinotecan.

In one embodiment, the invention comprises a method of treating recurrent locally advanced or metastatic gastric cancer in a human patient comprising administering a composition of the invention to the patient.

In one embodiment, the invention comprises a method of treating recurrent locally advanced or metastatic gastroesophageal junction adenocarcinoma in a human patient comprising administering a composition of the invention to the patient. In specific embodiments, the patient's tumor expresses PD-L1 [Combined Positive Score (CPS)≥1]. In specific embodiments, the patient has disease progression on or after two or more prior lines of therapy including fluoropyrimidine- and platinum-containing chemotherapy. In specific embodiments, the patient has disease progression on or after two or more prior lines of therapy including HER2/neu-targeted therapy.

In one embodiment, the invention comprises a method of treating recurrent locally advanced or metastatic squamous cell carcinoma of the esophagus in a human patient comprising administering a composition of the invention to the patient. In specific embodiments, the patient's tumor expresses PD-L1 [Combined Positive Score (CPS)≥1].

In one embodiment, the invention comprises a method of treating recurrent locally advanced or metastatic cervical cancer in a human patient comprising administering a composition of the invention to the patient. In specific embodiments, the patient's tumor expresses PD-L1 [Combined Positive Score (CPS)≥1].

In one embodiment, the invention comprises a method of treating hepatocellular carcinoma in a human patient comprising administering a composition of the invention to the patient. In one embodiment, the invention comprises a method of treating recurrent locally advanced or metastatic merkel cell carcinoma in a human patient comprising administering a composition of the invention to the patient. In one embodiment, the invention comprises a method of treating recurrent or metastatic cutaneous squamous cell carcinoma in a human patient comprising administering a composition of the invention to the patient.

In one embodiment, the invention comprises a method of treating advanced renal cell carcinoma in a human patient comprising administering a composition of the invention to the patient and axitinib. In one embodiment, the invention comprises a method of treating advanced endometrial carcinoma in a human patient comprising administering a composition of the invention to the patient and lenvatinib. In one embodiment, the endometrial carcinoma is not MSI-H or dMMR.

In one embodiment, the invention comprises a method of treating cancer in a human patient comprising administering a composition of the invention to the patient, wherein the patient has a cancer selected from the group consisting of: melanoma, lung cancer, head and neck cancer, bladder cancer, breast cancer, gastrointestinal cancer, multiple myeloma, hepatocellular cancer, lymphoma, renal cancer, mesothelioma, ovarian cancer, esophageal cancer, anal cancer, biliary tract cancer, colorectal cancer, cervical cancer, thyroid cancer, and salivary cancer.

In one embodiment, the invention comprises a method of treating small cell lung cancer in a human patient comprising administering a composition of the invention to the patient.

In one embodiment, the invention comprises a method of treating non-Hodgkin lymphoma in a human patient comprising administering a composition of the invention to the patient. In specific embodiments, the non-Hodgkin lymphoma is mediastinal large B-cell lymphoma. In specific embodiments, the non-Hodgkin lymphoma is diffuse large B-cell lymphoma.

In one embodiment, the invention comprises a method of treating breast cancer in a human patient comprising administering a composition of the invention to the patient. In certain embodiments, the breast cancer is triple negative breast cancer, optionally in combination with chemotherapy. In certain embodiments, the breast cancer is ER+/HER2– breast cancer. In specific embodiments, the patient's tumor expresses PD-L1 [Combined Positive Score (CPS)≥1].

In one embodiment, the invention comprises a method of treating nasopharyngeal cancer in a human patient comprising administering a composition of the invention to the patient.

In one embodiment, the invention comprises a method of treating thyroid cancer in a human patient comprising administering a composition of the invention to the patient.

In one embodiment, the invention comprises a method of treating salivary cancer in a human patient comprising administering a composition of the invention to the patient.

As noted above, in some embodiments of the methods of the invention, the method further comprises administering an additional therapeutic agent. In particular embodiments, the additional therapeutic agent is an anti-LAG3 antibody or antigen binding fragment thereof, an anti-GITR antibody, or antigen binding fragment thereof, an anti-TIGIT antibody, or antigen binding fragment thereof, an anti-CD27 antibody or antigen binding fragment thereof. In one embodiment, the additional therapeutic agent is a Newcastle disease viral vector expressing IL-12. In a further embodiment, the additional therapeutic agent is dinaciclib. In still further embodiments, the additional therapeutic agent is a STING agonist. In one embodiment, the additional therapeutic agent is Coxsakievirus CVA21.

Suitable routes of administration for the additional therapeutic agents may, for example, include parenteral delivery, including intramuscular, subcutaneous, as well as intrathecal, direct intraventricular, intravenous, intraperitoneal. Drugs can be administered in a variety of conventional ways, such as intraperitoneal, parenteral, intraarterial or intravenous injection.

Selecting a dosage of the additional therapeutic agent depends on several factors, including the serum or tissue turnover rate of the entity, the level of symptoms, the immunogenicity of the entity, and the accessibility of the target cells, tissue or organ in the individual being treated. The dosage of the additional therapeutic agent should be an amount that provides an acceptable level of side effects. Accordingly, the dose amount and dosing frequency of each additional therapeutic agent (e.g. biotherapeutic or chemotherapeutic agent) will depend in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Various literature references are available to facilitate selection of pharmaceutically acceptable carriers or excipients for the additional therapeutic agent. See, e.g., *Remington's Pharmaceutical Sciences* and *U.S. Pharmacopeia: National Formulary*, Mack Publishing Company, Easton, PA (1984); Hardman et al. (2001) *Goodman and Gilman's The Pharmacological Basis of Therapeutics*, McGraw-Hill, New York, NY; Gennaro (2000) *Remington: The Science and Practice of Pharmacy*, Lippincott, Williams, and Wilkins, New York, NY; Avis et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY.

A pharmaceutical antibody composition can be administered by continuous infusion, or by doses at intervals of, e.g., one day, 1-7 times per week, one week, two weeks, three weeks, monthly, bimonthly, etc. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

In certain embodiments, dosing will comprise administering to a subject escalating doses of 1.0, 3.0, and 10 mg/kg of the pharmaceutical composition or a composition of the invention, over the course of treatment. The composition can be a reconstituted liquid composition, or it can be a liquid composition not previously lyophilized. Time courses can vary, and can continue as long as desired effects are obtained. In certain embodiments, dose escalation will continue up to a dose of about 10 mg/kg. In certain embodiments, the subject will have a histological or cytological diagnosis of melanoma, or other form of solid tumor, and in certain instances, a subject may have non-measurable disease. In certain embodiments, the subject will have been treated with other chemotherapeutics, while in other embodiments, the subject will be treatment naïve.

In yet additional embodiments, the dosing regimen will comprise administering a dose of 1, 3, or 10 mg/kg of any of the pharmaceutical compositions or compositions described herein, throughout the course of treatment. For such a dosing regimen, the interval between doses will be about 14 days (±2 days). In certain embodiments, the interval between doses will be about 21 days (±2 days).

In certain embodiments, the dosing regimen will comprise administering a dose of from about 0.005 mg/kg to about 10 mg/kg, with intra-patient dose escalation. In certain embodiments, a dose of 5 mg/kg or 10 mg/kg will be administered at intervals of every 3 weeks, or every 2 weeks. In yet additional embodiments, a dose of 3 mg/kg will be administered at three week intervals for melanoma patients or patients with other solid tumors. In these embodiments, patients should have non-resectable disease; however, patients may have had previous surgery.

In certain embodiments, a subject will be administered a 30 minute IV infusion of any of the pharmaceutical compositions or compositions described herein. In certain embodiments for the escalating dose, the dosing interval will be about 28 days ((±1 day) between the first and second dose. In certain embodiments, the interval between the second and third doses will be about 14 days (±2 days). In certain embodiments, the dosing interval will be about 14 days (±2 days), for doses subsequent to the second dose. In certain embodiments, the dosing interval will be about 3 weeks, for doses subsequent to the second dose. In certain embodiments, the dosing interval will be about 6 weeks, for doses subsequent to the second dose.

In certain embodiments, the use of cell surface markers and/or cytokine markers, as described in WO2012/018538 or WO2008/156712 will be used in bioassays for monitoring, diagnostic, patient selection, and/or treatment regimens involving blockade of the PD-1 pathway. Subcutaneous administration may performed by injected using a syringe, or using other injection devices (e.g. the Inject-ease® device); injector pens; or needleless devices (e.g. MediJector and BioJector®).

Embodiments of the invention also include one or more of the biological compositions described herein (i) for use in, (ii) for use as a medicament or composition for, or (iii) for use in the preparation of a medicament for: (a) therapy (e.g., of the human body); (b) medicine; (c) induction of or increasing of an antitumor immune response (d) decreasing the number of one or more tumor markers in a patient; (e) halting or delaying the growth of a tumor or a blood cancer; (f) halting or delaying the progression of PD-1-related disease; (g) halting or delaying the progression of cancer; (h) stabilization of PD-1-related disease; (i) inhibiting the growth or survival of tumor cells; (j) eliminating or reducing the size of one or more cancerous lesions or tumors; (k) reduction of the progression, onset or severity of PD-1-related disease; (l) reducing the severity or duration of the clinical symptoms of PD-1-related disease such as cancer (m) prolonging the survival of a patient relative to the expected survival in a similar untreated patient n) inducing complete or partial remission of a cancerous condition or other PD-1 related disease, or o) treatment of cancer.

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, NY; Sambrook and Russell (2001) *Molecular Cloning, 3$^{rd}$ ed.*, Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current *Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, NY; Kontermann and Dubel (eds.) (2001) Antibody Engineering, Springer-Verlag, New York; Harlow and Lane (1988) *Antibodies A Laboratory Manual*, Cold Spring Harbor Laboratory Press, Cold Spring Harbor, NY, pp. 139-243; Carpenter, et al. (2000) *J Immunol.* 165:6205; He, et al. (1998) *J. Immunol.* 160:1029; Tang et al. (1999) J. Biol. Chem. 274:27371-27378; Baca et al. (1997) *J. Biol. Chem.* 272: 10678-10684; Chothia et al. (1989) *Nature* 342:877-883; Foote and Winter (1992) *J. Mol. Biol.* 224:487-499; U.S. Pat. No. 6,329,511).

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1: Continuous Perfusion Process

Glutamine Synthetase knock-out CHO host cell comprising a polynucleotide encoding a light chain with the amino acid sequence set forth in SEQ ID NO:5 and a polynucleotide encoding a heavy chain with the amino acid sequence set forth in SEQ ID NO:10 (expressing pembrolizumab) was used in the below procedures and Examples.

3 L Bioreactor Operation

Glass bioreactors (3 L, Sartorius Stedim, Göttingen, Germany) with a marine impeller (70 mm diameter) and a drilled hole sparger (14×holes with 0.5 mm diameter) were used. The bioreactors were inoculated at a target cell density of $0.5 \times 10^6$ cells/mL. Dissolved oxygen (DO) was controlled at 30-60% of air saturation using pure $O_2$ and agitation speed which was gradually increased in the range of 260-450 rpm to control $O_2$ sparge rate at <0.30 vvm to avoid excess foam formation. EX-CELL® antifoam (Sigma-Aldrich, St. Louis, MO) was added as needed for foam control. Overlay air was controlled at 0.1 L/min. Temperature was maintained at 36.5° C. throughout the culture duration. The pH of the bioreactor was controlled at 7.0±0.3 during the cultivation period.

A commercially available basal media was used for the initial bioreactor batch growth and subsequently a perfusion media was used for medium exchange. The perfusion media has a copper concentration of 10-35 ppb. Bioreactors started with a working volume of 1.6 L and maintained at the same level during perfusion. On day 3, when cell density reached between 2 to $4 \times 10^6$ cells/mL, medium exchange was started and the perfusion rate ramped up according to a predetermined schedule starting from 0.5 vvd. On day 4, the 1 vvd perfusion rate was applied and reached the maximum perfusion rate of 2 vvd between day 5 and end of the production. A TFF system with a magnetic levitating pump was used (KrosFlo® KML System, Repligen, Waltham, MA) for cell retention and medium exchange. The TFF system continuously circulates the cell culture fluid through a hollow fiber module while permeate was collected at the predetermined rates. The hollow fiber module specifications are as follows: module length: 32 cm; effective filtration surface area: 0.09 $m^2$; fiber lumen ID: 1.4 mm; pore size: 0.2 μm (Pall, Port Washington, NY). A TFF cross flow rate of 1.0 L/min was used in all experiments. Once the cell density reaches $100 \times 10^6$ cells/mL or capacitance target of 80 pF/cm, a cell bleed pump turns on to maintain the cell density or biovolume (capacitance, pF/cm Cell bleed was automatically controlled by a capacitance probe (Incyte DN12, Hamilton Bonaduz AG, Switzerland). Perfusion culture duration was 28-32 days. The copper concentration in the bioreactor ranged from 1 to 35 ppb. Continuous harvesting is started after day 5 when 2 vvd perfusion rate has been achieved for the bioreactor.

50 L Bioreactor Operation

The Xcellerx XDR 50 single use bioreactor (GE healthcare, Marlborough, MA) was used as a production bioreactor for this study. The bioreactor was inoculated at a target cell density of $0.5 \times 10^6$ cells/mL which dissolved oxygen (DO) controlled at 30-60% of air saturation using pure $O_2$ supply. The agitation of the bioreactor was controlled at the 86-93 rpm to ensure proper mixing and mass transfer. EX-CELL® antifoam (Sigma-Aldrich, St. Louis, MO) was added as needed for foam control. Overlay air was controlled at 0.1-0.5 L/min. Temperature was maintained at 36.5° C. throughout the culture duration. The pH of the bioreactor was controlled at 7.0±0.3 during the cultivation period.

A commercially available basal media was used for the initial bioreactor batch growth and subsequently a perfusion media was used for medium exchange. The perfusion media has a copper concentration of 32.5 ppb. Bioreactors started with a working volume of 50 L and maintained at the same level during perfusion. On day 3, when cell density reached between 2 to $4 \times 10^6$ cells/mL, medium exchange was started and the perfusion rate ramped up according to a predetermined schedule starting from 0.5 vvd at day 3, to 1 vvd at day 4 and reached the maximum perfusion rate of 2 vvd (0.5 day mean residence time) at day 5. A TFF system with a magnetic levitating pump was used (KrosFlo® KML System, Repligen, Waltham, MA) for cell retention and medium exchange. The TFF system continuously circulates the cell culture fluid through a hollow fiber module while permeate was collected at the pre-determined rates. The hollow fiber with pore size of 0.2 um ((Pall, Port Washington, NY) was used as a cell retention device for this study. A TFF cross flow rate of 10.5 L/min was used in this study. Once the cell density reaches $100-105 \times 10^6$ cells/mL or capacitance target of 80-85 pF/cm, a cell bleed pump turns on to maintain the cell density or biovolume (capacitance, pF/cm Cell bleed was automatically controlled by a capacitance probe (Incyte DN12, Hamilton Bonaduz AG, Switzerland) Perfusion culture duration was 28 days. Continuous harvesting started after day 5 when 2 vvd perfusion rate has been achieved for the bioreactor.

Samples were taken from the bioreactor and the permeate line daily. Viable cell density (VCD) and viability were measured using the trypan blue exclusion method on a Cedex Hi-Res cell counter (Roche Diagnostics GmbH, Mannheim, Germany). Cell diameter was determined on the same cell counter and reported. Offline pH, $pO_2$, and $pCO_2$ were measured using an ABL80 blood gas analyzer (Radiometer, Denmark). Glucose, lactate, ammonium, and lactate dehydrogenase (LDH) were measured using a RX Daytona+ or a Imola analyzer (Randox Laboratories, Ltd., Crumlin, UK). Bioreactor supernatant and permeate antibody titers were analyzed using an Agilent 1100 high-performance liquid chromatography (HPLC, Agilent Technologies, Santa Clara, CA) equipped with a Protein A column.

Example 2: Downstream Purification

Protein A Affinity Chromatography

Protein A affinity chromatography serves as the primary capture step, using MabSelect SuRe resin from GE Healthcare™ for the bulk of purification. The product binds to the resin, while impurities such as media components and host cell proteins are not bound and remain in the column flowthrough fraction. The protein A step is operated in a continuous manner using a continuous multi-column chromatography skid to allow for uninterrupted flow of HCCF from the bioreactor to feed the skid (BioSMB PD, Sartorius Stedim Biotech GmbH Goettingen Germany). This is achieved by utilizing 4 comparable columns packed with the same Protein A resin on the skid. At any one time, three columns are dedicated to loading while the fourth is undergoing the non-loading steps (equilibration step, washing steps, elution steps, regeneration steps) steps in the protein A method.

The HCCF from the bioreactor is connected to a continuous multi-column chromatography skid through a 3 L single-use surge vessel (Cercell, Herlev Denmark). The HCCF flow rate to the single use surge vessel matched the feed rate from the surge vessel to the continuous multi-column chromatography system maintaining a consistent volume in the vessel. The operational volume range in the surge vessel gave a 15-45 minute mean residence time of the fluid in the vessel with a target value of 30 minutes.

Operationally, the same steps are performed in multi-column Protein A chromatography as in single-column batch-mode chromatography including phases for column equilibration, loading, washing, and regeneration. After equilibrating the column with 10 mM Sodium Phosphate, pH 6.5 the loading phase was initiated. The protein was loaded to a capacity of 50 g/L of Protein A resin. The loading phase of the Protein A step was followed by three wash steps including: 10 mM Sodium Phosphate, pH 6.5, and 10 mM Sodium Phosphate with 0.5 M Sodium Chloride to elute loosely bound impurities and increase the purity of the antibody in the product stream. The product was eluted with 20 mM Sodium Acetate pH 3.6 via low pH shift and monitored by on-line spectrophotometry at an absorbance of 280 nm. The step in the surge vessel and the Protein A step was performed at ambient temperature (20±5° C.).

After Protein A chromatography, the protein was processed through additional purification and filtration steps to achieve the ultrafiltration product in a continuous process connected though intermediate surge vessels including: viral inactivation, depth filtration, anion exchange chromatography, virus filtration, single-pass tangential flow filtration, and in-line diafiltration.

Viral Inactivation/Depth Filtration

The Protein A affinity pool was adjusted with 1 M Acetic Acid to a low pH (target pH 3.6) to inactivate viruses that might be present. This step was performed at ambient temperature (20±5° C.). The pool after viral inactivation was adjusted with 1 M Tris to a target pH of 5.5 and is filtered through a charged depth filter (A1HC) and 0.22 µm filter for clarification (Millipore Sigma, Burlington MA). The filtered neutralized viral inactivation product (FNVIP) may be stored at 2-8° C. prior to further processing in the subsequent anion exchange chromatography step.

Anion Exchange

Anion exchange chromatography (AEX), performed with POROS HQ 50 from Applied Biosystems, is the first polishing step in the process. The pembrolizumab antibody flows through the column whereas residual impurities, such as host cell protein (HCP), DNA, aggregates, and virus that may be present are bound to the resin. The column was equilibrated and washed with 25 mM sodium phosphate pH 7.2. Prior to the start of the step, the post viral inactivation pool was pH adjusted with 1M Tris to a target pH of 7.2. The column effluent UV absorbance was monitored online at a wavelength of 280 nm and used to collect the AEX pool. The pool was pH adjusted with 1M Acetic Acid to pH 5.5 for continued processing in the post step surge vessel.

Viral Filtration

The AEX product was filtered through a 0.1 µm pre-filter or equivalent in-line with a Planova 20N (19 nm mean pore size) virus reduction filter (Asahi Kasei Bioprocess, Glenview, IL). The prefilter and filter connections were autoclaved and placed in line with the nanofilter in a biosafety cabinet. The filters were then flushed in series with 10 mM Histidine, 10 mM Methionine, pH 5.4 in a closed manner.

Ultrafiltration Concentration and Diafiltration

The viral filtration product was first concentrated 8× by a single-pass tangential flow filtration (SPTFF) module with a 30 kDa molecular weight cutoff (Pall Corporation Westboro MA Port Washington, NY). The product from the SPTFF step is then diafiltered with 10 mM Histidine, 10 mM Methionine, pH 5.4 resulting in a buffer exchange of the concentrated protein stream. A six-stage in-line diafiltration module (ILDF) unit containing 30 kDa MW cut-off membrane (Pall Corporation Westboro MA Port Washington, NY) was utilized to perform the buffer exchange. The diafiltration product, also referred to as the ultrafiltration product was further filtered through a sterile filter and collected into the storage containers. Once a sufficient mass of ultrafiltration product has been accumulated, the ultrafiltration product was pooled and was further concentrated by a standard batch ultrafiltration step using an Ultracel 30 kDa molecular weight cutoff membrane (Millipore, Burlington, MA) up to a final concentration of 190-200 g/L. Stock excipients were added to achieve a final drug substance formulation of 165 mg/mL in a 10 mM Histidine, 10 mM Methionine, 7% (w/v) sucrose, and 0.02% (w/v) PS-80 buffer pH 5.5.

Example 3: Method for Determining M105 Oxidation Levels

The oxidation levels of pembrolizumab was determined using the reduced peptide mapping mass spectrometry method outlined below.

Sample Preparation

In-process or Drug Substance (DS) samples were diluted with water to 5 mg/mL. A total of 20 µL, of the diluted sample (contains 100 µg) was denatured and reduced in final solution (100 µL) containing 6 M Guanidine-HCl, 50 µM Tris-HCl, 50 µM EDTA and 200 µM DTT. The mixed sample was incubated in thermomixer at 37° C. with 300 rpm shaking for 30 min. After mix and spin down, each sample is alkylated with 5 µL of iodoacetamide (IAM) (1 M) protected from light at 25° C. for 30 min. A total of 5 µL of DTT (200 µM) was added to block the unreacted iodoacetamide (IAM). Lysyl endopeptidase (Lys-C) (Wako, 125-05061) enzyme (1:10 (wt: wt)) in 500 µL was added to the protein sample with slowly pipette up/down 3 times to mix well. The digestion was incubated in a thermomixer at 37° C. for 60 min. The digestion is quenched with 15 µL, of 20% TFA. Digested sample was analyzed by LC-MS within 24 h after sample digestion. Otherwise, digested samples were stored at −80° C. for future analysis.

LC-MS Methods and Data Analysis

Figure 2:
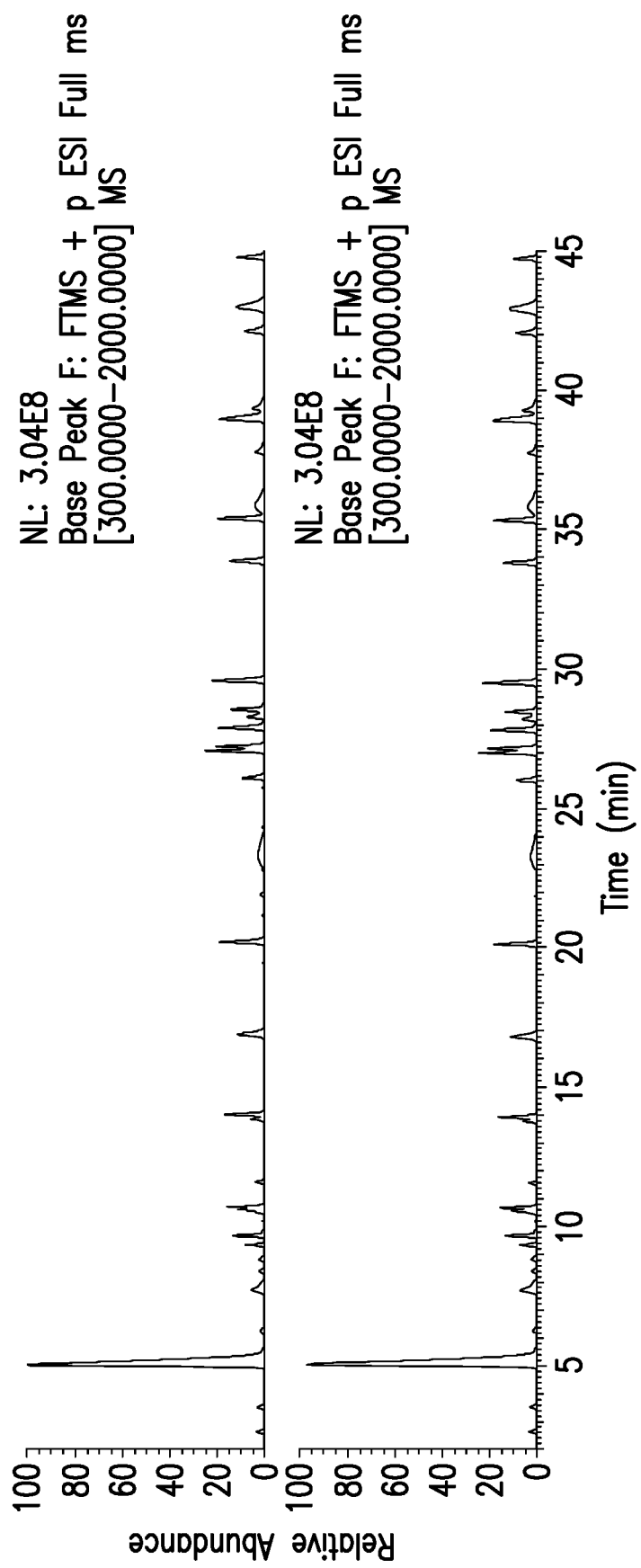
FIG. 2: The total ion chromatograms were generated by the reduced peptide digestion described in Example 3. Both fed batch produced pembrolizumab formulated drug product reference standard (top) and continuous perfusion produced pembrolizumab (bottom) were loaded similarly and the relative abundance shows identical peptides and retention times for both samples. NL refers to normalization level; m/z refers to mass over charge; FTMS refers to Fourier transform mass spectrometry, ESI refers to electrospray ionization.
Figure 3:
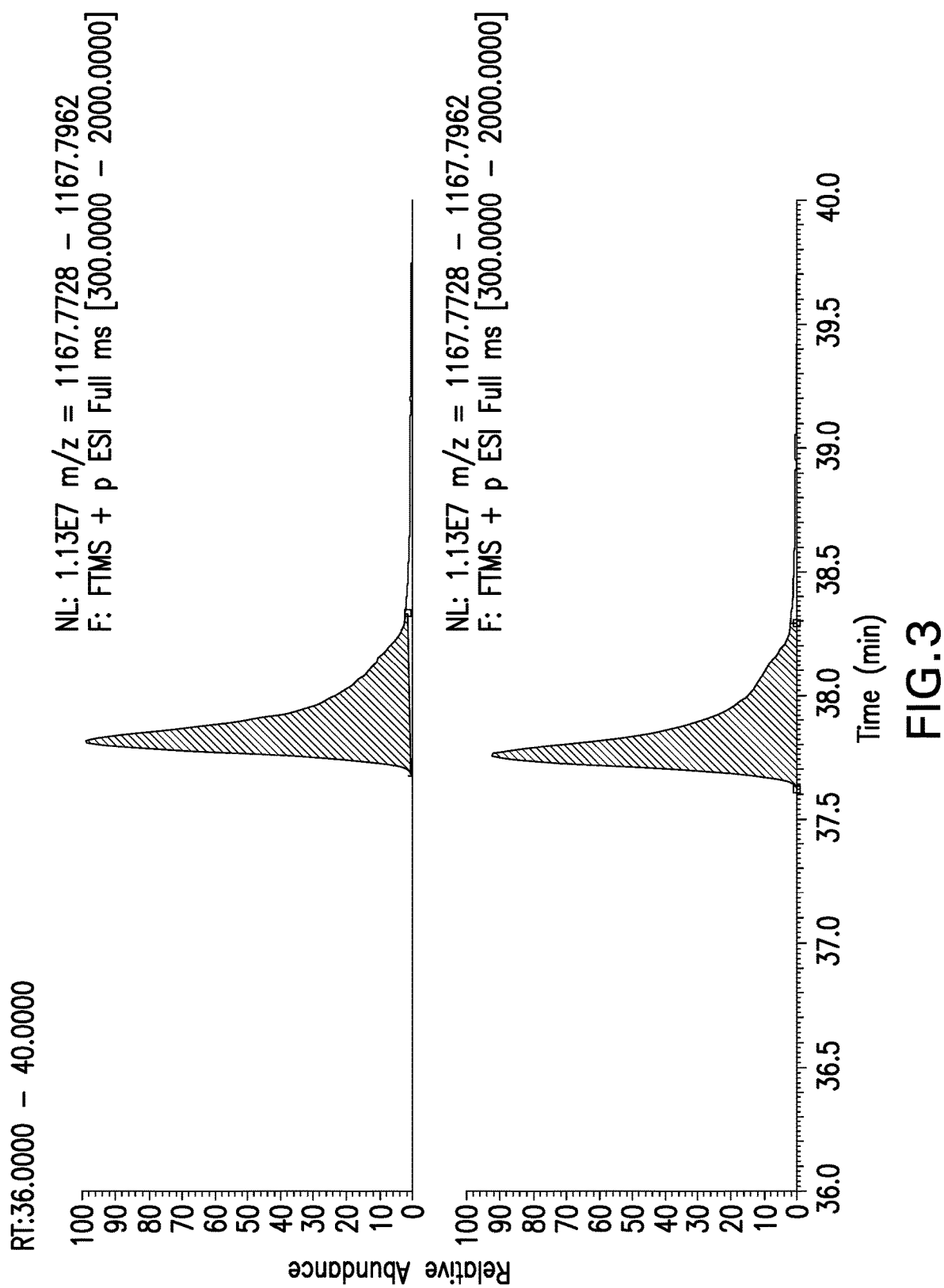
FIG. 3: The extracted ion chromatogram of the unmodified M105 peptide for fed batch produced pembrolizumab reference standard (top) and continuous perfusion produced pembrolizumab (bottom). The retention time of the unmodified peptide containing M105 is ~37.8 min. NL refers to normalization level; m/z refers to mass over charge; FTMS refers to Fourier transform mass spectrometry, ESI refers to electrospray ionization; RT refers to retention time.
Figure 4:
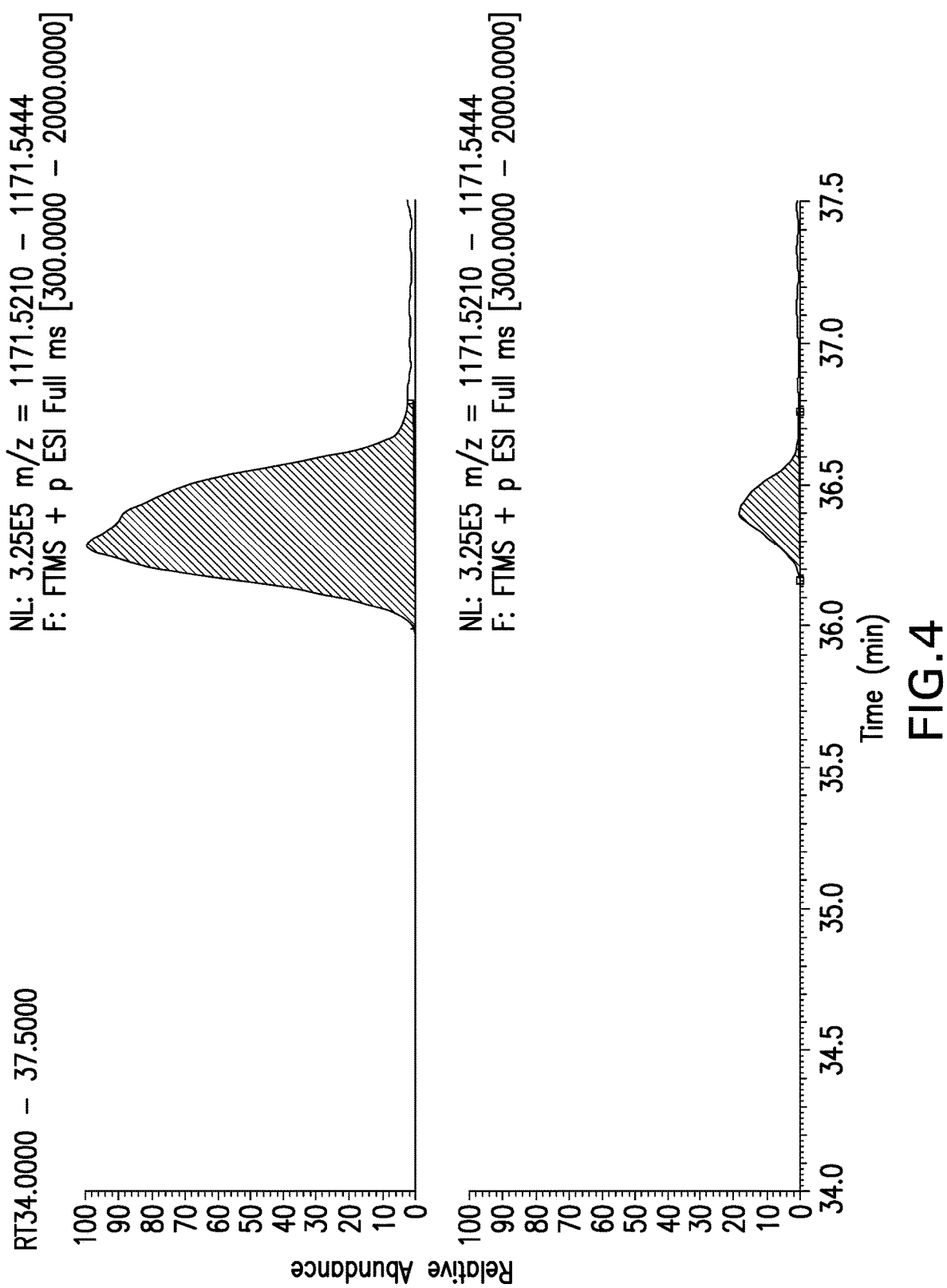
FIG. 4: The extracted ion chromatogram of the modified M105 peptide for fed batch produced pembrolizumab reference standard (top) and continuous perfusion produced pembrolizumab (bottom). The retention time of the modified peptide containing M105 is 36.4 min. NL refers to normalization level; m/z refers to mass over charge; FTMS refers to Fourier transform mass spectrometry, ESI refers to electrospray ionization. RT refers to retention time.

Waters Acquity Liquid Chromatography was used to inject 20 µL, of sample on the column (UPLC HSS T3 100 Å, 1.8 µm, 2.1 mm×150 mm, P/N:186003540). Autosampler was set at 5° C. Mobile phase A was 0.02% TFA in water and mobile phase B was 0.02% TFA in acetonitrile with a gradient of 0.1% B from 0 to 5 min, 0.1%-10% B from 5 to 7 min, followed by a linear increase to 35% B over the next 38 min. Q Exactive Orbitrap MS (Thermo) was used to collect the MS1 data. Chromeleon and Xcalibur was used for data analysis. The extracted ion chromatogram (EIC) of M105 non-modified and modified peptides (two charged states (+3 and +4) for each peptide and each with 3 isotopic ions) were used to determine the % M105 oxidation using the formula [peak area of the extracted ion chromatogram (EIC) of the modified peptide]/[peak area of EIC of the modified peptide+peak area of EIC of the unmodified peptide]×100. See FIGS. 2-4. The % CV (Coefficient of Variation; calculated as (standard deviation/mean)×100) for the M105 oxidation was less than 20%.

TABLE 3

| Sample | % M105 oxidation |
| --- | --- |
| Fed batch produced pembrolizumab formulated drug product reference standard | 4.9 |
| Continuous perfusion produced pembrolizumab Protein A purified product (Day 22) Batch 1 | 0.8 |
| Continuous perfusion produced pembrolizumab Ultrafiltered product (Day 22) Batch 1 | 0.6 |
| Continuous perfusion produced pembrolizumab Protein A product (Day 16) Batch 2 | 1.2 |
| Continuous perfusion produced pembrolizumab formulated Drug Substance (DS) | 1.3 |

The formulation for fed batch produced pembrolizumab drug product reference standard is 25 mg/mL pembrolizumab in 10 mM histidine buffer containing 7% (w/v) sucrose and 0.02% (w/v) polysorbate 80, pH 5.5. The formulation for continuous perfusion produced pembrolizumab formulated Drug Substance is 165 mg/mL pembrolizumab, 10 mM L-histidine, 7% (w/v) sucrose, 0.02% (w/v) PS80 and 10 mM L-Methionine, pH 5.5.

The % oxidized M105 for fed batch produced pembrolizumab formulated drug product reference standard was about 4.9% while the continuous perfusion produced pembrolizumab samples contain about 0.5%-3.0% M105. Some representative samples from protein A purification, ultrafiltered product (unformulated DS) and formulated DS are shown in Table 3.

Example 4: Measure Changes in M105 Oxidation of Pembrolizumab Over Time in HCCF

The rate of oxidation was determined by repeatedly measuring the amount of oxidation in a HCCF sample according to Example 1 by ProA-HIC 2D-LC as described below.

A sample was taken from the bioreactor and filtered to remove the cells, giving HCCF. Under sterile conditions, the HCCF sample was split into 200 μL aliquots across 48 wells of a 96 well plate. The plate was covered with an aluminum foil lid to retain sterility and shield the samples from light. The samples were immediately placed into an Agilent 1290 autosampler set at 25° C., with the internal light turned off. Each well of sample was analyzed in sequence by a two-dimensional liquid chromatography separation according to the time course.

Figure 5:
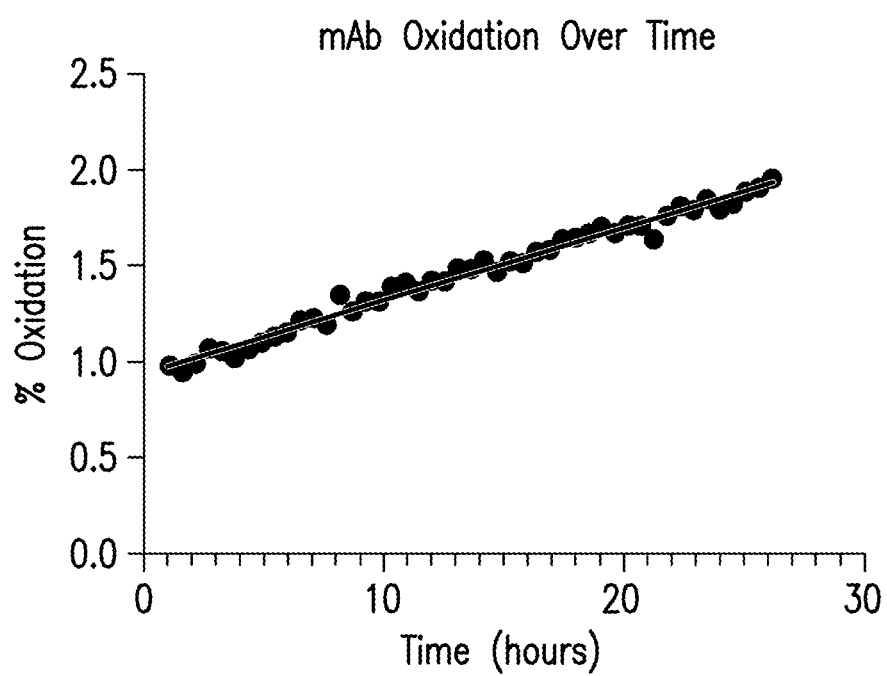
FIG. 5: Changes in M105 oxidation of pembrolizumab over time in Harvested Cell Culture Fluid (HCCF) samples. The black circles are the results of each sample injection, and the line is the linear fit of the data and is described by y=0.038x+0.94, with an R squared value of 0.9833.

The resultant chromatogram of each sample was integrated to determine the percent oxidation, and the summary of the data is shown in FIG. 5. The linear regression of the data shows the percent oxidation starting 0.94% and increasing at approximately 0.038% per hour over the next 26 hours to a maximum of 1.95% oxidation.

Example 5: Ion Exchange (Iex) Method to Measure Acidic Species of Anti-Pd-1 Antibodies For the IEX method, using a Waters Alliance LC system (Milford, MA, U.S.A.), the Thermo Scientific's ProPac WCX-10 (p/n: 054993, particle size 10 um, diameter 4 mm, length 250 mm) was chosen with a loading of 80 μg sample. Mobile Phase (A) 24 mM MES pH 6.1 with 4% acetonitrile, and mobile phase (B) 20 mM sodium phosphate, 95 mM NaCl pH 8.0 with 4% acetonitrile was used as a non-linear, sigmoidal shape, pH gradient, and the separation was monitored over 34 min with a flow rate of 0.5 mL min$^{-1}$, with the column temperature being 35° C. The gradient used was: 22%-22% B for 0-0.6 min; 22%-29% B for 0.6-15.0 min; 29%-70% B for 15.0-30.0 min; 70%-100% B for 30.0-30.5 min; and 100%-100% B from 30.5-33.0 min. Mobile phase (C) 10 mM CHES pH 8.0, 40 mM Tris, 15 mM EDTA, 200 mM NaCl, and 4% acetonitrile was used to strip the column at 0.5 mL min$^{-1}$ from 33.1-34.0 min, followed by re-equilibration with 22% B from 34.5-44.5 min at 1.0 mL min$^{-1}$. From 44.5-45 min, the flowrate was reduced to 0.5 mL min$^{-1}$. The elution was monitored at 280 nm for the detection of peaks. The assay variability was determined to be within 1%.

The chemical composition of each identified peak of the pembrolizumab reference sample was determined by collecting samples of each peak, and performing peptide mapping and reverse phase liquid chromatography followed by mass-spectrometry according to methods identical to those in Example 3 with analysis performed by MS/MS. The main peak was determined to predominantly contain the antibody with the amino acid sequence set forth in SEQ ID NO:5 and SEQ ID NO:11 for both light chains and heavy chains, respectively. Oxidation (for example, Methionine105) and deamidation of asparagine residues (for example, N31, N52, N55, N59 or N61 in the heavy chain of SEQ ID NO: 11) of the foregoing antibody was detected in the Acidic Variants peak. Deamidation of asparagine residues (for example, N384, N389 or N390 in the heavy chain of SEQ ID NO: 11) of the foregoing antibody was detected in the Acidic1 peak. In the Basic 1 peak, antibodies with one heavy chain consisting of the amino acid sequence of SEQ ID NO: 11, one heavy chain consisting of the amino acid sequence of SEQ ID NO: 12, and two light chains consisting of the amino acid sequence of SEQ ID NO: 5; or one heavy chain consisting of the amino acid sequence of SEQ ID NO: 11, one heavy chain consisting of the amino acid sequence of SEQ ID NO: 14, wherein the C-terminal leucine is alpha-amidated, and two light chains consisting of the amino acid sequence of SEQ ID NO: 5 were detected.

Figure 8:
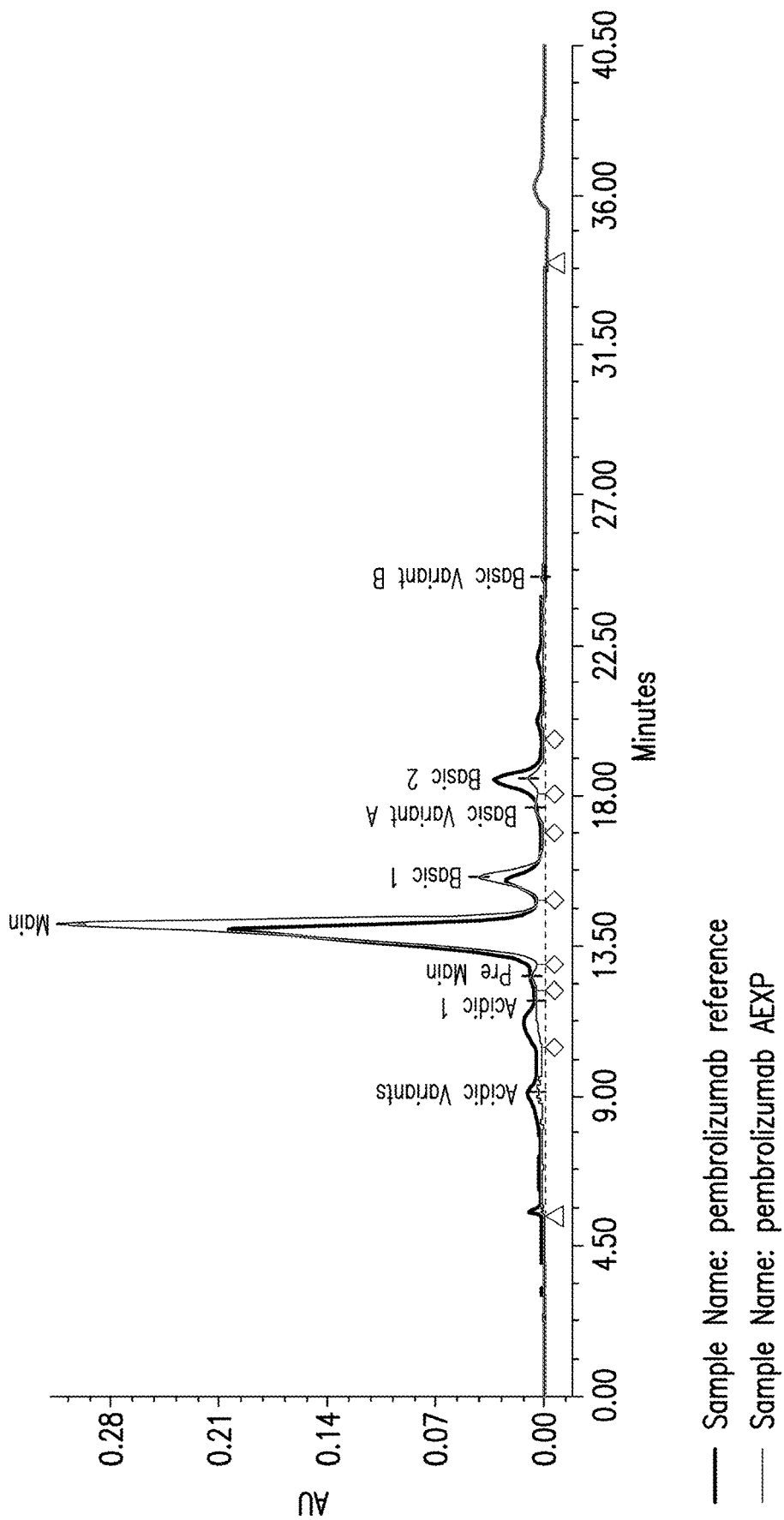
FIG. 8: Overlay of Ion exchange chromatography analytical diagram of pembrolizumab after Anion exchange step of the invention and pembrolizumab reference standard obtained from fed-batch method. The diamonds delineate the start and end of the integrated peak.
Figure 9:
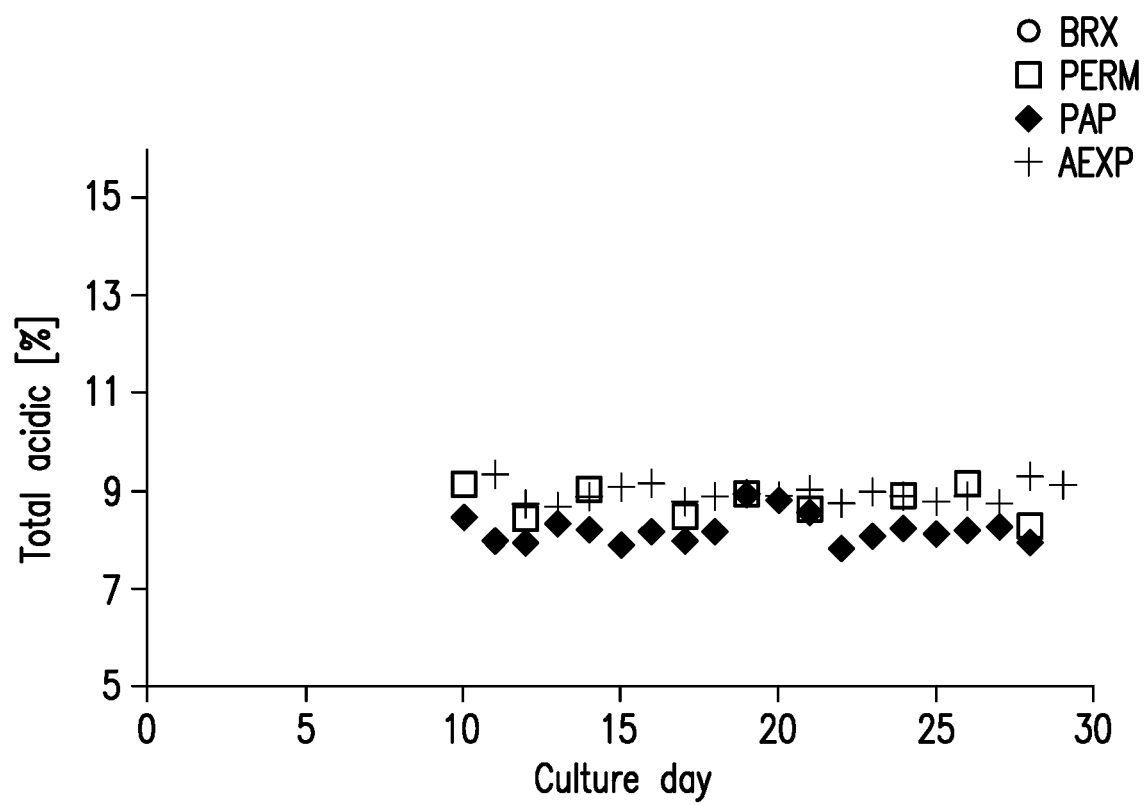
FIG. 9: Total % acidic species (acidic1+acidic variants+pre-main) in the cell culture fluid of the bioreactor (BRX), cell-free permeate (PERM), after Protein A chromatography step (PAP), after anion exchange chromatography (AEXP) in a time course by culture days.
Figure 10:
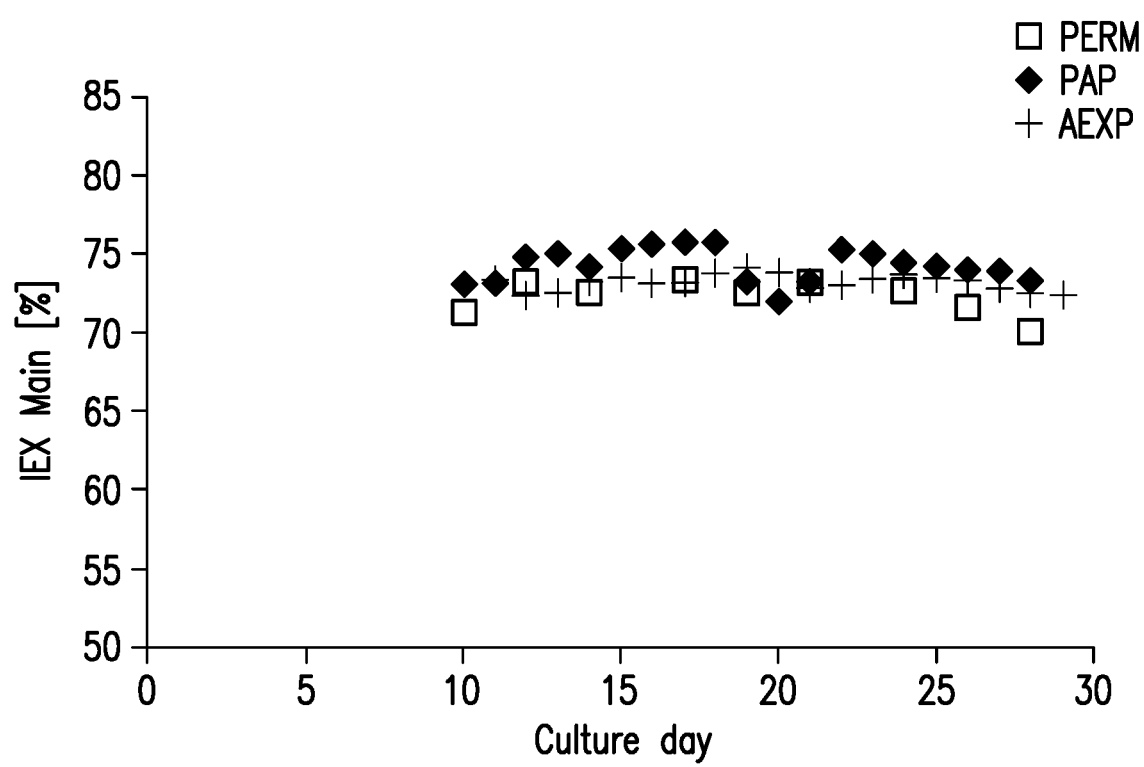
FIG. 10: Total % main species (as measured by ion exchange) in the cell-free permeate (PERM), after Protein A chromatography step (PAP), after anion exchange chromatography (AEXP) in a time course by culture days.
Figure 11:
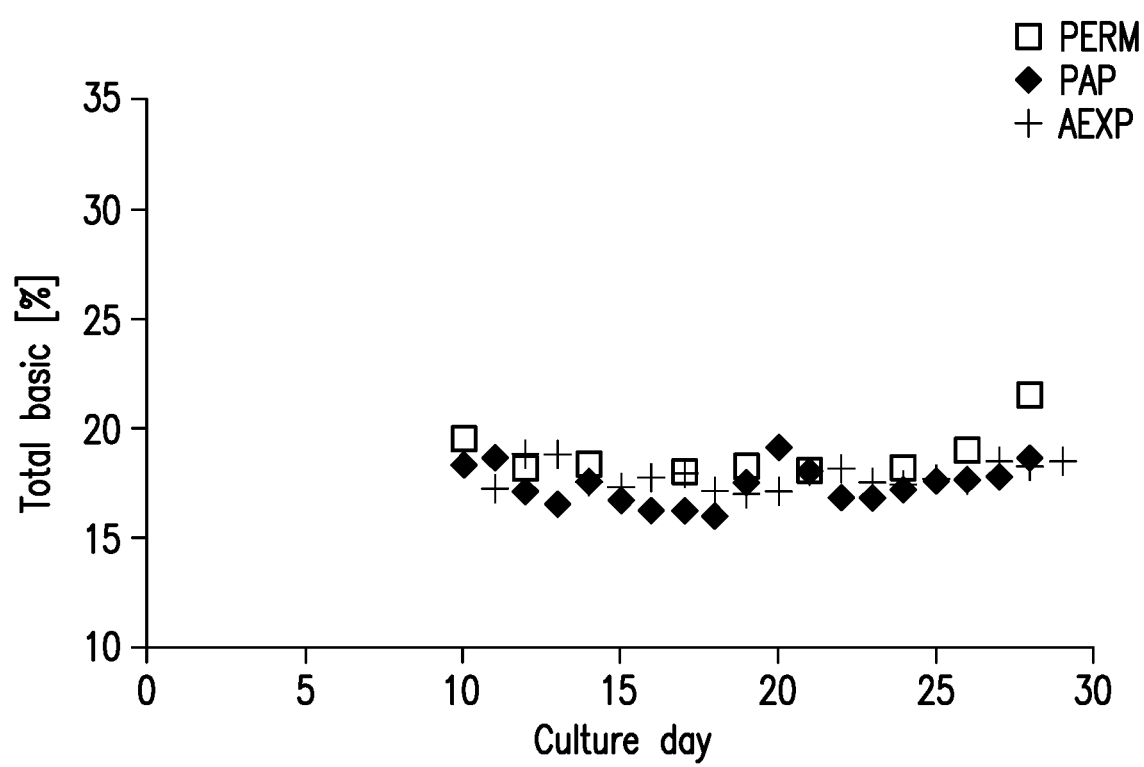
FIG. 11: Total % basic species (basic1+basic2+basic variant A+basic variant B) in the cell-free permeate (PERM), after Protein A chromatography step (PAP), after anion exchange chromatography (AEXP) in a time course by culture days.
Figure 12:
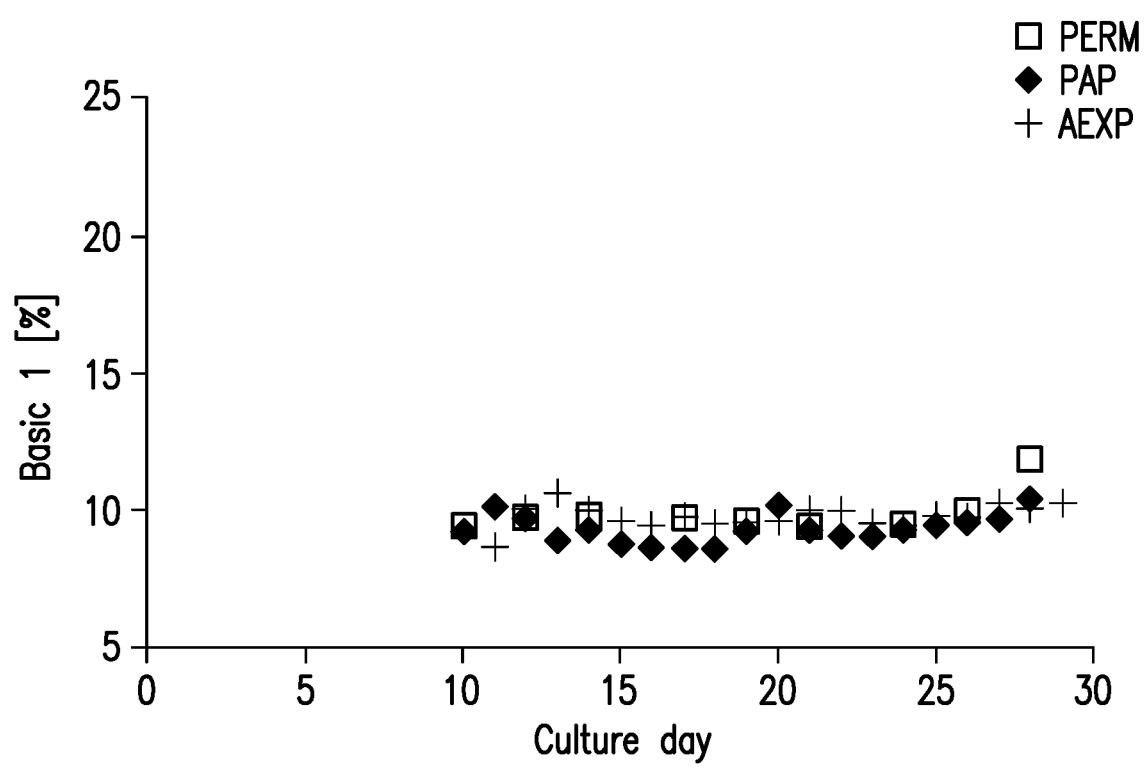
FIG. 12: % Basic1 species in the cell-free permeate (PERM), after Protein A chromatography step (PAP), after anion exchange chromatography (AEXP) in a time course by culture days.

The ion exchange chromatograms and % acidic species, main peak, and basic species from samples after Protein A chromatography (PAP) and Anion exchange chromatography (AEXP) according to procedures in Examples 1-2 are illustrated in FIGS. 6-7 and Table 4. The sum of the acidic species (acidic variants, Acidic 1 and Pre-Main) for the PAP and AEXP samples are 7.86% and 8.76% respectively. The sum of the basic species (basic 1, basic variant A, basic2, basic variant B) for the PAP and AEXP samples are 16.95%, 18.19% respectively. The ion exchange chromatograms and % acidic species, main peak, and basic species from pembrolizumab reference obtained by fed-batch method are illustrated in FIG. 8 and Table 5. The sum of the acidic species (acidic variants, Acidic 1 and Pre-Main) for the reference sample is 16.56%. The sum of the basic species (basic 1, basic variant A, basic2, basic variant B) for the reference sample is 23.76%. The sum of the basic variants (basic variant A and basic variant B) for the reference sample is 6.23%. In summary, the pembrolizumab samples prepared by the continuous perfusion process of the invention had higher percentage of main species due to lower percentage of acidic species in the mixture. In other batches of pembrolizumab samples prepared by the continuous perfusion process substantially similar to Examples 1-2, the main peak is about 74-80%.

TABLE 4

Pembrolizumab obtained from the methods of the invention: acidic, main and basic species

| Sample Name | Acidic Variants | Acidic 1 | Pre Main | Main | Basic 1 | Basic Variant A | Basic 2 | Basic Variant B | Basic Variants (Sum A + B) |
|---|---|---|---|---|---|---|---|---|---|
| PAP-D22 | 3.12 | 2.67 | 2.07 | 75.2 | 9 | 1.69 | 2.55 | 3.71 | 5.4 |
| AEXP-D22 | 3.77 | 3 | 1.99 | 73.05 | 9.96 | 1.86 | 2.72 | 3.65 | 5.51 |

TABLE 5

Pembrolizumab reference acidic, main and basic species

| Name | Retention Time | % Area |
|---|---|---|
| Acidic Variants | 9.546 | 8.1 |
| Acidic 1 | 10.513 | 6.41 |
| Pre Main | 11.79 | 2.05 |
| Main | 13.269 | 59.68 |
| Basic 1 | 14.726 | 8.07 |
| Basic Variant A | 16.782 | 1.36 |
| Basic 2 | 17.743 | 9.46 |
| Basic Variant B | 21.795 | 4.87 |

FIGS. 9-12 also provide a time course for the % total acidic species, % main species, % total basic species and % basic 1 species in cell-free permeate (PERM), after Protein A chromatography step (PAP), after anion exchange chromatography (AEXP) prepared according to procedures in Examples 1-2 in a time course by culture days.

U.S. provisional application No. 63/143,461 is incorporated by reference in its entirety. All references cited herein are incorporated by reference to the same extent as if each individual publication, database entry (e.g. Genbank sequences or GeneID entries), patent application, or patent, was specifically and individually indicated to be incorporated by reference each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. To the extent that the references provide a definition for a claimed term that conflicts with the definitions provided in the instant specification, the definitions provided in the instant specification shall be used to interpret the claimed invention.

What is claimed is:

1. A method of obtaining a purified composition comprising anti-human PD-1 antibodies or antigen-binding fragments thereof, wherein the anti-human PD-1 antibodies or antigen binding fragments thereof comprise a light chain variable region comprising three light chain CDRs comprising CDRL1 of SEQ ID NO:1, CDRL2 of SEQ ID NO:2 and CDRL3 of SEQ ID NO:3 and a heavy chain variable region comprising three heavy chain CDRs of CDRH1 of SEQ ID NO:6, CDRH2 of SEQ ID NO:7 and CDRH3 SEQ ID NO:8, comprising the steps of:
   a) perfusing Chinese Hamster Ovary host cells in cell culture medium in a perfusion bioreactor by providing fresh medium at a rate of at least about 0.25-6.0 vessel volume per day (vvd), wherein the host cell comprises a polynucleotide encoding the light chain variable domain and a polynucleotide encoding the heavy chain variable domain, or a polynucleotide encoding the light chain variable domain and the heavy chain variable domain, of the anti-human PD-1 antibodies or antigen-binding fragments thereof, wherein a cell culture broth is formed in the perfusion bioreactor;
   b) continuously harvesting the antibodies or antigen-binding fragments thereof from the cell culture broth to obtain a harvest cell culture fluid medium at a rate of at least about 0.25-6.0 vessel volume per day (vvd); and
   c) continuously purifying the harvest cell culture fluid with an affinity chromatography step to obtain the purified composition.

2. The method of claim 1, wherein the perfusion maintains a capacitance value of 70-90 pF/cm.

3. The method of claim 1, wherein in step b), the rate is about 0.5 vvd on Day 3, about 1 vvd on Day 4 and about 2 vvd on Day 5, and the purified composition Is obtained from step c) on or after Day 5.

4. The method of claim 1, wherein in step a) the perfusion is initiated when the cell density reaches about 2 to $10 \times 10^6$ cells/ml.

5. The method of claim 1, wherein in step a) the perfusion is initiated when the cell density reaches about 4 to $8 \times 10^6$ cells/ml.

6. The method of claim 1, wherein in step b), the rate is at about 0.5 vvd to 4 vvd.

7. The method of claim 2, wherein in step b), the rate is at about 0.5 vvd to 4 vvd.

8. The method of claim 1, wherein in step b), the continuous harvesting is initiated after a perfusion rate reaches about 2 vvd.

9. The method of claim 2, wherein in step b), the continuous harvesting is initiated after a perfusion rate reaches about 2 vvd.

10. The method of claim 8, wherein the cell culture medium comprises copper, and the copper concentration in the perfusion bioreactor ranges from 1 to 35 ppb.

11. The method of claim 1, wherein the continuous harvesting is performed by setting a constant permeate rate to obtain a cell-free permeate through a hollow fiber membrane connected to the perfusion bioreactor.

12. The method of claim 1, wherein between steps (b) and (c), the method further comprises the step of: transferring the harvest cell culture fluid (HCCF) to a surge vessel for a residence time of about 0.5 to 30 hours.

13. The method of claim 2, wherein between steps (b) and (c), the method further comprises the step of: transferring the harvest cell culture fluid (HCCF) to a surge vessel for a residence time of about 0.5 to 30 hours.

14. The method of claim 8, wherein between steps (b) and (c), the method further comprises the step of: transferring the harvest cell culture fluid (HCCF) to a surge vessel for a mean residence time of 15 to 45 minutes.

15. The method of claim 9, wherein between steps (b) and (c), the method further comprises the step of: transferring the harvest cell culture fluid (HCCF) to a surge vessel for a mean residence time of 15 to 45 minutes.

16. The method of claim 8, wherein the affinity chromatography step is Protein A affinity chromatography.

17. The method of claim 9, wherein the affinity chromatography step is Protein A affinity chromatography.

18. The method of claim 16, wherein between steps (b) and (c), the method further comprises the step of: transferring the harvest cell culture fluid (HCCF) to a surge vessel for a mean residence time of 15 to 45 minutes.

19. The method of claim 16, wherein the affinity chromatography is operated in a continuous multi-column chromatography system.

20. The method of claim 17, wherein the affinity chromatography is operated in a continuous multi-column chromatography system.

21. The method of claim 18, wherein the affinity chromatography is operated in a continuous multi-column chromatography system.

22. The method of claim 20, wherein the affinity chromatography is fluidly connected to the perfusion bioreactor of step a).

23. The method of claim 12, wherein a surge vessel is fluidly connected to the perfusion bioreactor and affinity chromatography, and the HCCF flow rate to the surge vessel equals the feed rate from the surge vessel to the continuous multi-column chromatography system.

24. The method of claim 1, wherein the anti-human PD-1 antibodies or antigen binding fragments thereof comprise a light chain variable region comprising the amino acid sequence set forth in SEQ ID NO:4, and a heavy chain variable region comprising the amino acid sequence set forth in SEQ ID NO:9.

25. The method of claim 8, wherein the purified composition comprises anti-human PD-1 antibodies, wherein the anti-human PD-1 antibodies consist of two light chains and two heavy chains, wherein the two light chains consist of the amino acid sequence set forth in SEQ ID NO:5, wherein the two heavy chains consist of the amino acid sequence set forth in any one of SEQ ID NO: 10-15, or a combination thereof.

26. The method of claim 9, wherein the purified composition comprises anti-human PD-1 antibodies, wherein the anti-human PD-1 antibodies consist of two light chains and two heavy chains, wherein the two light chains consist of the amino acid sequence set forth in SEQ ID NO:5, wherein the two heavy chains consist of the amino acid sequence set forth in any one of SEQ ID NO: 10-15, or a combination thereof.

27. The method of claim 21, wherein the purified composition comprises anti-human PD-1 antibodies, wherein the anti-human PD-1 antibodies consist of two light chains and two heavy chains, wherein the two light chains consist of the amino acid sequence set forth in SEQ ID NO:5, wherein the two heavy chains consist of the amino acid sequence set forth in any one of SEQ ID NO:10-15, or a combination thereof.

28. The method of claim 1, wherein the antibody is a pembrolizumab.

29. The method of claim 1, wherein the antibody is a pembrolizumab variant.

30. A method of obtaining a purified composition comprising anti-human PD-1 antibodies or antigen-binding fragments thereof, wherein the anti-human PD-1 antibodies or antigen binding fragments thereof comprise a light chain variable region comprising three light chain CDRs comprising CDRL1 of SEQ ID NO:1, CDRL2 of SEQ ID NO:2 and CDRL3 of SEQ ID NO:3 and a heavy chain variable region comprising three heavy chain CDRs of CDRH1 of SEQ ID NO:6, CDRH2 of SEQ ID NO:7 and CDRH3 SEQ ID NO:8, comprising the steps of:

a) perfusing Chinese Hamster Ovary host cells in cell culture medium in a perfusion bioreactor by applying a perfusion rate of at least about 0.25-6.0 vessel volume per day (vvd), wherein the host cell comprises a polynucleotide encoding the light chain variable domain and a polynucleotide encoding the heavy chain variable domain, or a polynucleotide encoding the light chain variable domain and the heavy chain variable domain, of the anti-human PD-1 antibodies or antigen-binding fragments thereof, wherein a cell culture broth is formed in the perfusion bioreactor;

b) continuously harvesting the antibodies or antigen-binding fragments thereof from the cell culture broth to obtain a harvest cell culture fluid;

c) transferring the harvest cell culture fluid (HCCF) to a surge vessel for a mean residence time of 15 to 45 minutes, or a residence time of about 0.5 to 30 hours; and d) continuously purifying the harvest cell culture fluid with an affinity chromatography step to obtain the purified composition.

31. The method of claim 30, wherein the affinity chromatography is a continuous multi-column Protein A chromatography system.

32. The method of claim 31, wherein the purified composition comprises anti-human PD-1 antibodies, wherein the anti-human PD-1 antibodies consist of two light chains and two heavy chains, wherein the two light chains consist of the amino acid sequence set forth in SEQ ID NO:5, wherein the two heavy chains consist of the amino acid sequence set forth in any one of SEQ ID NOs:10-15, or a combination thereof.

* * * * *